(12) United States Patent
Halac et al.

(10) Patent No.: US 11,504,031 B2
(45) Date of Patent: Nov. 22, 2022

(54) SYSTEMS AND METHODS FOR POWER MANAGEMENT IN ANALYTE SENSOR SYSTEM

(71) Applicant: DexCom, Inc., San Diego, CA (US)

(72) Inventors: Jason Halac, San Diego, CA (US); Douglas William Burnette, Winnetka, CA (US); John Michael Gray, San Diego, CA (US); Carl Erich Hoffmeier, Solana Beach, CA (US); Neal Davis Johnston, San Diego, CA (US); Neel Narayan Shah, Carlsbad, CA (US); Liang Wang, La Jolla, CA (US); Riley Christopher Yaylian, San Diego, CA (US)

(73) Assignee: Dexcom, Inc., San Diego, CA (US)

( * ) Notice: Subject to any disclaimer, the term of this patent is extended or adjusted under 35 U.S.C. 154(b) by 92 days.

(21) Appl. No.: 16/402,820

(22) Filed: May 3, 2019

(65) Prior Publication Data
US 2019/0336048 A1 Nov. 7, 2019

Related U.S. Application Data

(60) Provisional application No. 62/667,348, filed on May 4, 2018.

(51) Int. Cl.
*A61B 5/145* (2006.01)
*A61B 5/00* (2006.01)
(Continued)

(52) U.S. Cl.
CPC .......... *A61B 5/145* (2013.01); *A61B 5/0002* (2013.01); *A61B 5/0004* (2013.01);
(Continued)

(58) Field of Classification Search
CPC ........ A61B 2560/0209; A61B 5/14532; A61B 5/0002; A61B 5/746; A61B 5/0015;
(Continued)

(56) References Cited

U.S. PATENT DOCUMENTS

| 4,992,987 A | 2/1991 | Echols et al. |
| 5,445,609 A | 8/1995 | Lattin et al. |

(Continued)

FOREIGN PATENT DOCUMENTS

| EP | 1682203 B1 | 1/2010 |
| EP | 2636372 A1 | 9/2013 |

(Continued)

OTHER PUBLICATIONS

Communication pursuant to Article 94(3) EPC for European Application No. 19796346.5, dated Dec. 11, 2020, 3 pages.

(Continued)

*Primary Examiner* — Eric F Winakur
*Assistant Examiner* — Alice Ling Zou
(74) *Attorney, Agent, or Firm* — Patterson + Sheridan, LLP

(57) ABSTRACT

An analyte sensor system may include a first communication circuit configured to transmit a wireless signal in a first communication mode and a second communication mode, and a processor, wherein the processor determines whether a first condition is satisfied, the first condition relating to the sensor signal or to communication by the first communication circuit, and shifts the system to a second communication mode responsive to the first condition being satisfied.

8 Claims, 14 Drawing Sheets

(51) Int. Cl.
  *H04W 52/02* (2009.01)
  *H01M 50/543* (2021.01)
  *H04W 12/06* (2021.01)
  *A61B 5/1486* (2006.01)
  *A61B 5/1495* (2006.01)

(52) U.S. Cl.
  CPC ............ *A61B 5/0015* (2013.01); *A61B 5/681* (2013.01); *A61B 5/6801* (2013.01); *A61B 5/6831* (2013.01); *H01M 50/543* (2021.01); *H04W 12/06* (2013.01); *H04W 52/02* (2013.01); *H04W 52/0232* (2013.01); *A61B 5/0022* (2013.01); *A61B 5/0031* (2013.01); *A61B 5/1486* (2013.01); *A61B 5/1495* (2013.01); *A61B 5/14532* (2013.01); *A61B 5/14546* (2013.01); *A61B 5/6833* (2013.01); *A61B 2560/0209* (2013.01); *A61B 2560/0214* (2013.01); *A61B 2560/0223* (2013.01); *A61B 2560/0443* (2013.01); *H01M 2220/30* (2013.01)

(58) Field of Classification Search
  CPC ................ A61B 5/002; A61B 5/0024; A61B 2560/0271; A61B 5/4839; A61B 5/14865; A61B 2560/0204; A61B 5/14546; A61B 5/1455; A61B 5/1459; A61B 5/1486; A61B 2560/0266; H04W 52/02; G16H 40/63; G16H 40/67; A61M 5/1723; A61M 2005/1726; A61M 2205/3303; A61M 2205/35; A61M 2205/3546; A61M 2205/3561–3592

See application file for complete search history.

(56) References Cited

U.S. PATENT DOCUMENTS

| | | | |
|---|---|---|---|
| 5,669,790 | A | 9/1997 | Carson et al. |
| 6,001,067 | A | 12/1999 | Shults et al. |
| 6,424,847 | B1 | 7/2002 | Mastrototaro et al. |
| 6,477,395 | B2 | 11/2002 | Schulman et al. |
| 6,484,046 | B1 | 11/2002 | Say et al. |
| 6,512,939 | B1 | 1/2003 | Colvin et al. |
| 6,565,509 | B1 | 5/2003 | Say et al. |
| 6,579,690 | B1 | 6/2003 | Bonnecaze et al. |
| 6,749,587 | B2 | 6/2004 | Flaherty et al. |
| 7,756,561 | B2 | 7/2010 | Reggiardo et al. |
| 7,885,697 | B2 | 2/2011 | Brister et al. |
| 7,949,381 | B2 | 5/2011 | Brister et al. |
| 8,512,276 | B2 * | 8/2013 | Talbot ................ A61M 5/1723 604/65 |
| 8,929,963 | B2 * | 1/2015 | Lisogurski ........... A61B 5/7271 600/310 |
| 2003/0100821 | A1 | 5/2003 | Heller et al. |
| 2004/0122353 | A1 * | 6/2004 | Shahmirian ......... A61M 5/1723 700/282 |
| 2005/0027462 | A1 | 2/2005 | Goode, Jr. et al. |
| 2005/0027463 | A1 | 2/2005 | Goode, Jr. et al. |
| 2005/0065464 | A1 * | 3/2005 | Talbot ..................... A61B 5/01 600/316 |
| 2006/0020186 | A1 | 1/2006 | Brister et al. |
| 2006/0020187 | A1 | 1/2006 | Brister et al. |
| 2006/0036142 | A1 | 2/2006 | Brister et al. |
| 2007/0027385 | A1 | 2/2007 | Brister et al. |
| 2007/0197890 | A1 | 8/2007 | Boock et al. |
| 2007/0212906 | A1 | 9/2007 | Clayton et al. |
| 2007/0254593 | A1 * | 11/2007 | Jollota ................... G16H 20/17 455/67.11 |
| 2008/0108942 | A1 | 5/2008 | Brister et al. |
| 2008/0119703 | A1 | 5/2008 | Brister et al. |
| 2008/0139910 | A1 | 6/2008 | Mastrototaro et al. |
| 2008/0312512 | A1 * | 12/2008 | Brukalo ............... G16H 20/17 600/300 |
| 2009/0089999 | A1 | 4/2009 | Say et al. |
| 2009/0105636 | A1 * | 4/2009 | Hayter ................. A61B 5/7221 604/66 |
| 2009/0216100 | A1 * | 8/2009 | Ebner ............... H04W 52/0216 600/347 |
| 2010/0168545 | A1 | 7/2010 | Kamath et al. |
| 2010/0330935 | A1 | 12/2010 | Maggert et al. |
| 2011/0058485 | A1 * | 3/2011 | Sloan ..................... G16H 40/67 370/242 |
| 2011/0181127 | A1 | 7/2011 | Safabakhsh |
| 2011/0191044 | A1 | 8/2011 | Stafford |
| 2012/0059231 | A1 | 3/2012 | Frey et al. |
| 2012/0078071 | A1 | 3/2012 | Böet al. |
| 2012/0082879 | A1 | 4/2012 | Petrie et al. |
| 2013/0103424 | A1 | 4/2013 | Brown |
| 2013/0150691 | A1 | 6/2013 | Pace et al. |
| 2013/0267811 | A1 | 10/2013 | Pryor et al. |
| 2013/0344813 | A1 | 12/2013 | Ebner et al. |
| 2014/0066730 | A1 | 3/2014 | Roesicke et al. |
| 2014/0121989 | A1 | 5/2014 | Kamath et al. |
| 2014/0266776 | A1 * | 9/2014 | Miller .................. A61B 5/6849 340/870.01 |
| 2014/0273645 | A1 | 9/2014 | Glick et al. |
| 2015/0094559 | A1 | 4/2015 | Russell |
| 2015/0164392 | A1 | 6/2015 | Taub et al. |
| 2015/0289788 | A1 | 10/2015 | Simpson et al. |
| 2016/0058375 | A1 | 3/2016 | Rothkopf |
| 2016/0058380 | A1 | 3/2016 | Lee et al. |
| 2016/0198988 | A1 | 7/2016 | Bhavaraju et al. |
| 2017/0020456 | A1 | 1/2017 | Pace |
| 2017/0112534 | A1 | 4/2017 | Schoonmaker et al. |
| 2017/0181628 | A1 | 6/2017 | Burnette et al. |
| 2017/0188910 | A1 | 7/2017 | Halac et al. |
| 2017/0188912 | A1 | 7/2017 | Halac et al. |
| 2017/0251922 | A1 | 9/2017 | Roesicke et al. |
| 2017/0290533 | A1 | 10/2017 | Antonio et al. |
| 2018/0027412 | A1 * | 1/2018 | Mandapaka ........... A61B 5/742 713/151 |
| 2018/0110078 | A1 | 4/2018 | Mandapaka et al. |
| 2018/0116572 | A1 | 5/2018 | Simpson et al. |
| 2019/0125224 | A1 * | 5/2019 | Kamath ................ H04W 12/06 |
| 2019/0184093 | A1 * | 6/2019 | Sjolund ................ A61B 5/7435 |
| 2019/0336049 | A1 | 11/2019 | Shah et al. |
| 2019/0336054 | A1 | 11/2019 | Shah et al. |
| 2019/0336055 | A1 | 11/2019 | Shah et al. |

FOREIGN PATENT DOCUMENTS

| | | | |
|---|---|---|---|
| EP | 1606758 B1 * | 11/2015 | ............ A61B 5/002 |
| EP | 2179754 B1 | 6/2016 | |
| GB | 2452158 A | 2/2009 | |
| WO | WO 2003/026726 | 4/2003 | |
| WO | WO-2017127349 A1 | 7/2017 | |

OTHER PUBLICATIONS

Communication pursuant to Rules 161 (2) and 162 EPC for EP Application No. 19796159.2, dated Dec. 11, 2020, 3 pages.
International Search Report and Written opinion for Application No. PCT/US2019/030719 dated Sep. 11, 2019, 13 pages.
International Search Report and Written Opinion dated Sep. 30, 2019 for Application No. PCT/US2019/030745.

* cited by examiner

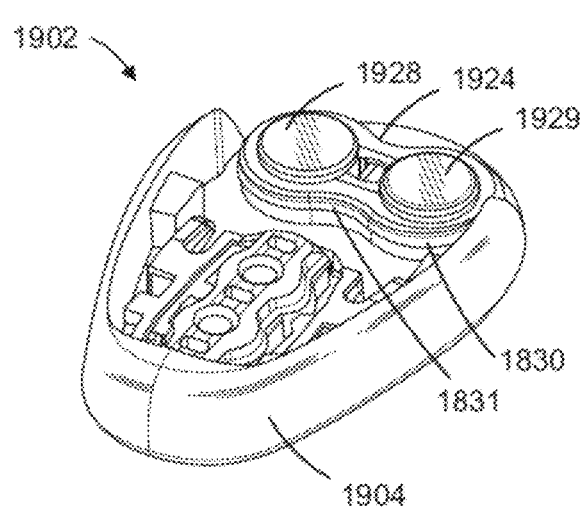
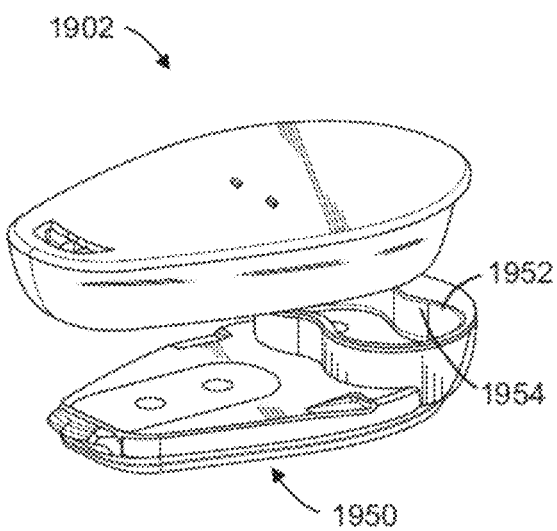
FIG. 19A
FIG. 19B
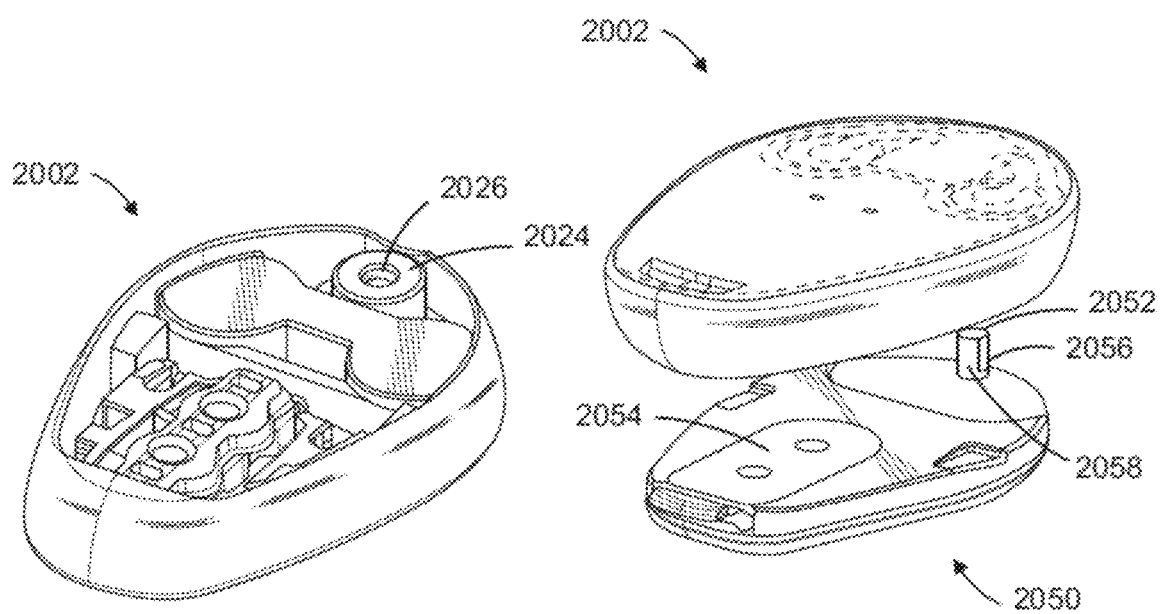
FIG. 20A
FIG. 20B

SYSTEMS AND METHODS FOR POWER MANAGEMENT IN ANALYTE SENSOR SYSTEM

INCORPORATION BY REFERENCE TO RELATED APPLICATION

Any and all priority claims identified in the Application Data Sheet, or any correction thereto, are hereby incorporated by reference under 37 CFR 1.57. This application claims the benefit of U.S. Provisional Application No. 62/667,348, filed May 4, 2018. The aforementioned application is incorporated by reference herein in its entirety, and is hereby expressly made a part of this specification.

TECHNICAL FIELD

The present development relates generally to medical devices such as analyte sensors, and more particularly, but not by way of limitation, to systems, devices, and methods to manage power consumption in analyte sensors.

BACKGROUND

Diabetes is a metabolic condition relating to the production or use of insulin by the body. Insulin is a hormone that allows the body to use glucose for energy, or store glucose as fat.

When a person eats a meal that contains carbohydrates, the food is processed by the digestive system, which produces glucose in the person's blood. Blood glucose can be used for energy, or stored as fat. The body normally maintains blood glucose levels in a range that provides sufficient energy to support bodily functions and avoids problems that can arise when glucose levels are too high, or too low. Regulation of blood glucose levels depends on the production and use of insulin, which regulates the movement of blood glucose into cells.

When the body does not produce enough insulin, or when the body is unable to effectively use insulin that is present, blood sugar levels can elevate beyond normal ranges. The state of having a higher than normal blood sugar level is called "hyperglycemia." Chronic hyperglycemia can lead to a number of health problems, such as cardiovascular disease, cataract and other eye problems, nerve damage (neuropathy), and kidney damage. Hyperglycemia can also lead to acute problems, such as diabetic ketoacidosis—a state in which the body becomes excessively acidic due to the presence of blood glucose and ketones, which are produced when the body cannot use glucose. The state of having lower than normal blood glucose levels is called "hypoglycemia." Severe hypoglycemia can lead to acute crises that can result in seizures or death.

A diabetes patient can receive insulin to manage blood glucose levels. Insulin can be received, for example, through a manual injection with a needle. Wearable insulin pumps are also available. Diet and exercise also affect blood glucose levels. A glucose sensor can provide an estimated glucose concentration level, which can be used as guidance by a patient or caregiver.

Diabetes conditions are sometimes referred to as "Type 1" and "Type 2". A Type 1 diabetes patient is typically able to use insulin when it is present, but the body is unable to produce sufficient amounts of insulin, because of a problem with the insulin-producing beta cells of the pancreas. A Type 2 diabetes patient may produce some insulin, but the patient has become "insulin resistant" due to a reduced sensitivity to insulin. The result is that even though insulin is present in the body, the insulin is not sufficiently used by the patient's body to effectively regulate blood sugar levels.

Blood sugar concentration levels may be monitored with an analyte sensor, such as a continuous glucose monitor. A wearable continuous glucose monitor may be powered by a battery that powers the sensor and other components, such as wireless communication circuitry. It is important that battery power be consistently available to assure that analyte concentration levels can be sensed and communicated by the analyte sensor.

This Background is provided to introduce a brief context for the Summary and Detailed Description that follow. This Background is not intended to be an aid in determining the scope of the claimed subject matter nor be viewed as limiting the claimed subject matter to implementations that solve any or all of the disadvantages or problems presented above.

SUMMARY

This document discusses, among other things, systems, devices, and methods for battery management in an analyte sensor, such as a glucose sensor.

An example (e.g., "Example 1") of subject matter (e.g., a method, device or system) may include an analyte sensor configured to generate a sensor signal representative of an analyte concentration level of a host, a first communication circuit configured to transmit a wireless signal in a first communication mode and a second communication mode, and a processor, wherein the processor determines whether a first condition is satisfied, the first condition relating to the sensor signal or to communication by the first communication circuit, and shifts the system to a second communication mode responsive to the first condition being satisfied.

An example (e.g., "Example 2") of subject matter (e.g., a method, device or system) may include an analyte sensor configured to generate a sensor signal representative of an analyte concentration level, a nonvolatile memory circuit, and a processor configured to receive the sensor signal, wherein the processor periodically saves information into the nonvolatile memory circuit to enable retrieval and use or communication of the information after a power reset.

An example (e.g., "Example 3") of subject matter (e.g., a method, device or system) may include monitoring one or more physiologic sensor values determined from a sensor signal received from the analyte sensor, monitoring one or more communication performance metrics pertaining to communication to or from the wearable sensor device, and increasing or decreasing power output of the communication circuit based at least in part upon the monitored physiologic sensor values and the communication performance metrics.

An example (e.g., "Example 4") of subject matter (e.g., a method, device or system) may include a base configured to connect to a host, a reusable portion, and a battery assembly. The base may include an analyte sensor configured to detect a sensor signal indicative of an analyte concentration level of the host. The reusable portion may be configured to couple to the base may include a wireless transceiver, wherein the reusable portion receives a signal from the base and transmits a wireless signal based at least in part on the sensor signal. The battery assembly may include a battery housing and one or more batteries. The battery assembly may be configured to mechanically couple with the base or the reusable portion and electrically couple with the base or the reusable portion, wherein the batteries deliver power to the analyte sensor and the wireless transceiver.

An example (e.g., "Example 5") of subject matter (e.g., a method, device or system) may include a sensor electronics package including a processor and a communication circuit, and a plurality of sensor devices, each sensor device including a sensor device battery and a sensor configured to generate a signal indicative of an analyte concentration level of a host, wherein the sensor electronics package is configured to electrically and mechanically couple with each of the plurality of sensor devices and draw power from the sensor device battery to power the processor and the communication circuit, wherein the sensor electronics package is reusable with the plurality of sensor devices.

An example (e.g., "Example 6") of subject matter (e.g., a method, device or system) may include an analyte sensor configured to generate a sensor signal representative of an analyte concentration level, a communication circuit, and a processor operatively coupled to the analyte sensor and the communication circuit, wherein the processor receives the sensor signal, determines one or more values based on the sensor signal, and transmits the one or more values to a peripheral device via the communication circuit, and wherein the processor receives via the communication circuit an operational parameter from the peripheral device, and controls the system using the operational parameter.

An example (e.g., "Example 7") of subject matter (e.g., a method, device or system) may include a rechargeable battery, an analyte sensor configured to generate a signal a sensor signal representative of a concentration level of a substance in a fluid of a host, a processor configured to receive the sensor signal and determine a value based on the sensor signal, wherein the processor is powered by the rechargeable battery, and a recharge circuit configured to receive energy and recharge the battery using the received energy. In various examples, the recharge circuit may include a triboelectric charging circuit, a piezoelectric charging circuit, an RF charging circuit, a light charging circuit, an ultrasonic charging circuit, a heat charging circuit, a heat harvesting circuit, or a circuit that harvests energy from the communication circuit. In some examples, the recharging circuit may recharge the rechargeable battery using power supplied from a replaceable battery (e.g., a battery supplied with a base component.)

An example (e.g., "Example 8") of subject matter (e.g., a method, device or system) may include an analyte sensor configured to generate a signal a sensor signal representative of a concentration level of a substance in a fluid of a host, a processor configured to receive the sensor signal and determine a value based on the sensor signal, a communication circuit operatively coupled to the processor and configured to transmit the value based on the sensor signal, a battery, and a supercapacitor electrically coupled to the battery, wherein the battery and the supercapacitor are configured to deliver power to the processor or the communication circuit, the supercapacitor reducing a load on the battery to reduce strain on the battery during a high-load period.

An example (e.g., "Example 9") of subject matter (e.g., a system or apparatus) may optionally combine any portion or combination of any portion of any one or more of Examples 1-8 to include "means for" performing any portion of any one or more of the functions or methods of Examples 1-8.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 19A is a perspective top view of an example sensor base.

FIG. 19B is a perspective bottom view of the base shown in FIG. 19A and an example sensor electronics module configured to mechanically and electrically couple with the base shown in FIGS. 19A and 19B.

FIG. 20A is a perspective top view of an example sensor base.

FIG. 20B is a perspective bottom view of the base shown in FIG. 20A and an example sensor electronics module configured to mechanically and electrically couple with the base shown in FIGS. 20A and 20B.

DETAILED DESCRIPTION

Figure 1:
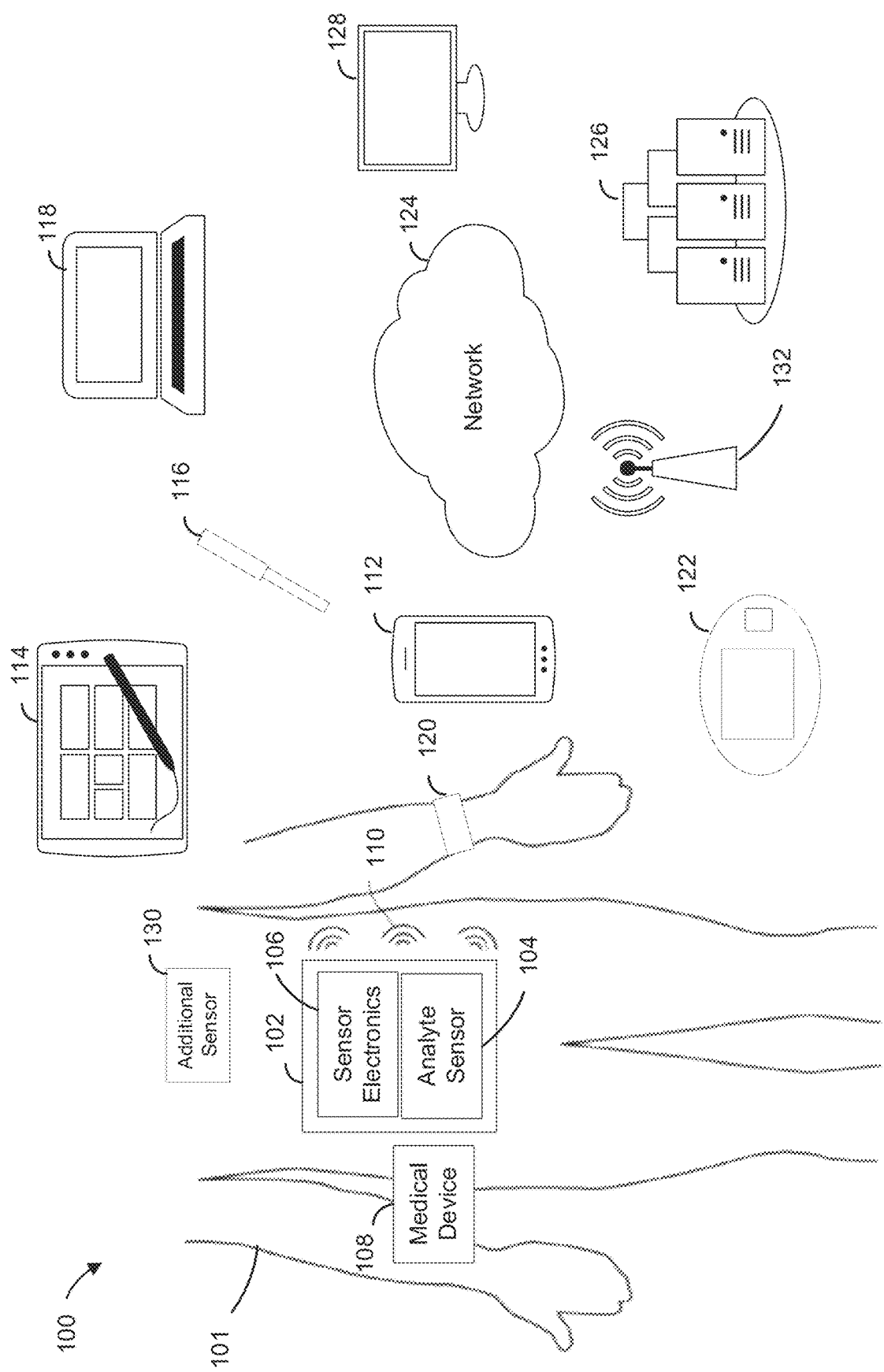
FIG. 1 is an illustration of an example medical device system.

The present inventors have recognized, among other things, that methods and devices may be applied to manage the energy available to analyte sensor systems. For example, the consumption of energy stored in batteries or other devices may be managed by controlling the amount of energy consumed by an analyte sensor system. The operation of an analyte monitoring device or system may be improved by managing battery power to extend the life of battery-powered portions of the system and assure that communication is available when needed.

In other examples, replaceable batteries may be provided to assure energy is available or to extend the life of a system components such as a sensor electronics package.
Overview Energy in an analyte sensor system may be managed by controlling energy output, such as the consumption of energy by communication circuits or other circuits, and by controlling energy inputs, such as replacing or recharging batteries. Wearable analyte sensor systems may include a battery, capacitor, or other power storage component, that powers a sensor, processor, communication circuit, or other electrical components. Management of energy consumption (e.g. power management, i.e. management of energy expended per unit of time) can be important to extend the life of sensor components (e.g., a battery) and to assure that the analyte sensor continues to perform its intended function(s). For example, where a component (e.g., a sensor electronics module, which may include relatively costly wireless sensor electronics package components) has a battery that is not rechargeable or replaceable, the life of the component may be extended by managing the use of energy stored in the battery.

Sensor systems may apply algorithms that take into account one or more of a variety of real-time, systemic, trend, model, or other factors such as wireless performance, analyte management (e.g., glucose management), battery state, power management trends or characteristic, patient or environmental risk factors, risk tolerance, location, or a combination thereof. For example, a system may take an action responsive to a condition. A system response may include changing system behavior to decrease power consumption or increase power consumption based on the determined condition. For example, an analyte management condition (e.g., estimated glucose level in range or below or above a specified value or exhibiting a specified trend) may be used as an input to determine system behavior and energy consumption. In various examples, a condition may be predetermined and programmed or hard-wired into a device, or specified by a user, or determined by a processor (e.g., based upon information learned from data.)

In some examples, a sensor system may receive an operational parameter that relates to a peripheral device, which may be a therapy device such as an insulin pump or pen. The sensor system may receive the operational parameter from the peripheral device, or from a remote resource based on an identification of the peripheral device (e.g., pump model number or serial number), or from a memory (e.g., retrieved from a lookup table.) The sensor system may manage its operations based at least in part on the operational parameter. For example, based on the operational parameter, a system may communicate according to a schedule, or with a specified device or group of devices, or manage power consumption to extend a battery.

System hardware may be configured to enable replacement of batteries, and system components (e.g., sensor base and sensor electronics) may be configured to provide a water-tight seal after replacement of batteries. Battery-supporting technologies such as supercapacitors may also be used to facilitate energy management.
Example System FIG. 1 is an illustration of an example system 100. The system 100 may include an analyte sensor system 102 that may be coupled to a host 101. The host 101 may be a human patient. The patient may, for example, be subject to a temporary or permanent diabetes condition or other health condition for which analyte monitoring may be useful.

The analyte sensor system 102 may include an analyte sensor 104, which may for example be a glucose sensor. The glucose sensor may be any device capable of measuring the concentration of glucose. For example, the analyte sensor 104 may be fully implantable, or the analyte sensor may be wearable on the body (e.g., on the body but not under the skin), or the analyte sensor may be a transcutaneous device (e.g., with a sensor residing under or in the skin of a host). It should be understood that the devices and methods described herein can be applied to any device capable of detecting a concentration of glucose and providing an output signal that represents the concentration of glucose (e.g., as a form of analyte data).

The analyte sensor system 102 may also include sensor electronics 106. In some examples, the analyte sensor 104 and sensor electronics 106 may be provided as an integrated package. In other examples, the analyte sensor 104 and sensor electronics 106 may be provided as separate components or modules. For example, the analyte sensor system 102 may include a disposable (e.g., single-use) base that may include the analyte sensor 104, a component for attaching the sensor to a host (e.g., an adhesive pad), or a mounting structure configured to receive another component. The system may also include a sensor electronics package, which may include some or all of the sensor electronics 106 shown in FIG. 2. The sensor electronics package may be reusable.

An analyte sensor may use any known method, including invasive, minimally-invasive, or non-invasive sensing techniques (e.g., optically excited fluorescence, microneedle, transdermal monitoring of glucose), to provide a data stream indicative of the concentration of the analyte in a host. The data stream may be a raw data signal, which may be converted into a calibrated and/or filtered data stream that is used to provide a useful value of the analyte (e.g., estimated blood glucose concentration level) to a user, such as a patient or a caretaker (e.g., a parent, a relative, a guardian, a teacher, a doctor, a nurse, or any other individual that has an interest in the wellbeing of the host).

Analyte sensor 104 may, for example, be a continuous glucose sensor, which may, for example, include a subcutaneous, transdermal (e.g., transcutaneous), or intravascular device. In some embodiments, such a sensor or device may recurrently (e.g., periodically or intermittently) analyze sensor data. The glucose sensor may use any method of glucose-measurement, including enzymatic, chemical, physical, electrochemical, spectrophotometric, polarimetric, calorimetric, iontophoretic, radiometric, immunochemical, and the like. In various examples, the analyte sensor system 102 may be or include a continuous glucose monitor sensor available from DexCom™ (e.g., the DexCom G5™ sensor or Dexcom G6™ sensor or any variation thereof.)

In some examples, analyte sensor 104 may be an implantable glucose sensor, such as described with reference to U.S. Pat. No. 6,001,067 and U.S. Patent Publication No. US-2005-0027463-A1. In some examples, analyte sensor 104 may be a transcutaneous glucose sensor, such as described with reference to U.S. Patent Publication No. US-2006-0020187-A1. In some examples, analyte sensor 104 may be configured to be implanted in a host vessel or extracorporeally, such as is described in U.S. Patent Publication No. US-2007-0027385-A1, co-pending U.S. Patent Publication No. US-2008-0119703-A1 filed Oct. 4, 2006, U.S. Patent Publication No. US-2008-0108942-A1 filed on Mar. 26, 2007, and U.S. Patent Application No. US-2007-0197890-A1 filed on Feb. 14, 2007. In some examples, the continuous glucose sensor may include a transcutaneous sensor such as described in U.S. Pat. No. 6,565,509 to Say et al., for example. In some examples, analyte sensor 104 may be a continuous glucose sensor that includes a subcutaneous sensor such as described with reference to U.S. Pat. No. 6,579,690 to Bonnecaze et al. or U.S. Pat. No. 6,484,046 to Say et al., for example. In some examples, the continuous glucose sensor may include a refillable subcutaneous sensor such as described with reference to U.S. Pat. No. 6,512,939 to Colvin et al., for example. The continuous glucose sensor may include an intravascular sensor such as described with reference to U.S. Pat. No. 6,477,395 to Schulman et al., for example. The continuous glucose sensor may include an intravascular sensor such as described with reference to U.S. Pat. No. 6,424,847 to Mastrototaro et al., for example.

The system 100 may also include a second medical device 108, which may, for example, be a drug delivery device (e.g., insulin pump or insulin pen). In some examples, the medical device 108 may be or include a sensor, such as another analyte sensor, a heart rate sensor, a respiration sensor, a motion sensor (e.g. accelerometer), posture sensor (e.g. 3-axis accelerometer), acoustic sensor (e.g. to capture ambient sound or sounds inside the body). In some examples, medical device 108 may be wearable, e.g. on a watch, glasses, contact lens, patch, wristband, ankle band, or other wearable item, or may be incorporated into a handheld device (e.g., a smartphone). In some examples, the medical device 108 may include a multi-sensor patch that may, for example, detect one or more of an analyte level (e.g. glucose, lactate, insulin or other substance), heart rate, respiration (e.g., using impedance), activity (e.g. using an accelerometer), posture (e.g. using an accelerometer), galvanic skin response, tissue fluid levels (e.g. using impedance or pressure).

The analyte sensor system 102 may communicate with the second medical device 108 via a wired connection, or via a wireless communication signal 110. For example, the analyte sensor system may be configured to communicate using via radio frequency (e.g. Bluetooth, Medical Implant Communication System (MICS), WiFi, NFC, RFID, Zigbee, Z-Wave or other communication protocols), optically (e.g. infrared), sonically (e.g. ultrasonic), or a cellular protocol (e.g., CDMA (Code Division Multiple Access) or GSM (Global System for Mobiles), or wired connection (e.g. serial, parallel, etc.). In some examples, an array or network of sensors may be associated with the patient. For example, the analyte sensor system 102, medical device 108, and an additional sensor 130 may communicate with one another via wired or wireless (e.g., Bluetooth, MICS, or any of the other options discussed above,) communication. The additional sensor 130 may be any of the examples discussed above with respect to medical device 108. The analyte sensor system 102, medical device 108, and additional sensor 130 on the host 101 are provided for the purpose of illustration and discussion and are not necessarily drawn to scale.

The system may also include one or more peripheral devices, such as a hand-held smart device (e.g., smartphone) 112, tablet 114, smart pen 116 (e.g., insulin delivery pen with processing and communication capability), computer 118, watch 120, or peripheral medical device 122, any of which may communicate with the analyte sensor system 102 via a wireless communication signal, and may also communicate over a network 124 with a server system (e.g., remote data center) 126 or with a remote terminal 128 to facilitate communication with a remote user (not shown) such as a technical support staff member or a clinician.

The system 100 may also include a wireless access point (WAP) 132 that may be used to communicatively couple one or more of analyte sensor system 102, network 124, server system 126, medical device 108 or any of the peripheral devices described above. For example, WAP 132 may provide Wi-Fi and/or cellular connectivity within system 100. Other communication protocols (e.g., Near Field Communication (NFC) or Bluetooth) may also be used among devices of the system 100. In some examples, the server system 126 may be used to collect analyte data from analyte sensor system 102 and/or the plurality of other devices, and to perform analytics on collected data, generate or apply universal or individualized models for glucose levels, and communicate such analytics, models, or information based thereon back to one or more of the devices in the system 100.

Figure 2:
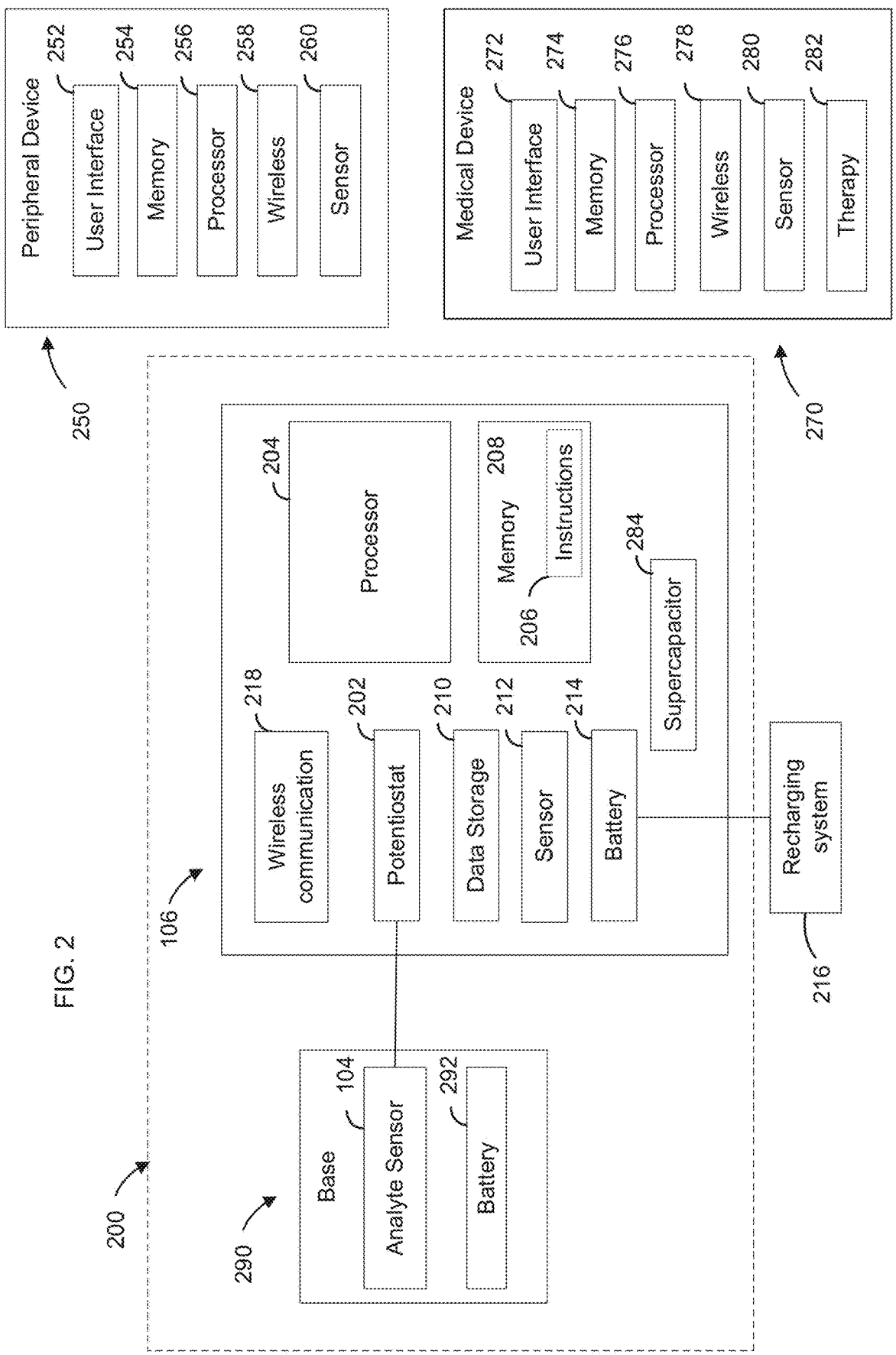
FIG. 2 is a schematic illustration of various example electronic components that may be part of the medical device system shown in FIG. 1.

FIG. 2 is a schematic illustration of various example electronic components that may be part of a medical device system 200. In an example, the system may include a sensor electronics 106 and a base 290. While a specific example of division of components between the base and sensor electronics is shown, it is understood that some examples may include additional components in the base 290 or in the sensor electronics 106, and the some of the components (e.g., supercapacitor 284) that are shown in the sensor electronics 106 may be alternative or additionally (e.g., redundantly) provided in the base. In an example, the base 290 may include the analyte sensor 104 and a battery 292. In some examples, the base may be replaceable, and the sensor electronics 106 may include a debouncing circuit (e.g., gate with hysteresis or delay) to avoid, for example, recurrent execution of a power-up or power down process when a battery is repeatedly connected and disconnected, or avoid processing of noise signal associated with removal or replacement of a battery.

The sensor electronics 106 may include electronics components that are configured to process sensor information, such as sensor data, and generate transformed sensor data and displayable sensor information. The sensor electronics 106 may, for example, include electronic circuitry associated with measuring, processing, storing, or communicating continuous analyte sensor data, including prospective algorithms associated with processing and calibration of the sensor data. The sensor electronics module 106 may include hardware, firmware, and/or software that enables measurement of levels of the analyte via a glucose sensor. Electronic components may be affixed to a printed circuit board (PCB), or the like, and can take a variety of forms. For example, the electronic components may take the form of an integrated circuit (IC), such as an Application-Specific Integrated Circuit (ASIC), a microcontroller, and/or a processor.

As shown in FIG. 2, the sensor electronics 106 may include a potentiostat 202, which may be coupled to the analyte sensor 104 and configured to recurrently obtain analyte sensor readings using the analyte sensor, for example by continuously or recurrently placing a voltage bias across sensor electrodes and measuring a current flow indicative of analyte concentration. The sensor electronics may also include a processor 204, which may retrieve instructions 206 from memory 208 and execute the instructions to determine control application of bias potentials to the analyte sensor 104 via the potentiostat, interpret signals from the sensor, or compensate for environmental factors. The processor may also save information in data storage memory 210, or retrieve information from data storage memory 210. In various examples, data storage memory 210 may be integrated with memory 208, or may be a separate memory circuit, such as a non-volatile memory circuit (e.g., flash RAM). Examples of systems and methods for processing sensor analyte data are described in more detail herein and in U.S. Pat. Nos. 7,310,544 and 6,931,327.

The sensor electronics 106 may also include a sensor 212, which may be coupled to the processor. The sensor 212 may, for example, be a temperature sensor or an accelerometer. The sensor electronics 106 may also include a power source such as a capacitor or battery 214, which may be integrated into the sensor electronics, or may be removable, or part of a separate electronics package. The battery 214 (or other power storage component, e.g., capacitor) may optionally be rechargeable via a wired or wireless (e.g., inductive or ultrasound) recharging system 216. The recharging system may harvest energy, or may receive energy from an external source or on-board source. In various examples, the recharge circuit may include a triboelectric charging circuit, a piezoelectric charging circuit, an RF charging circuit, a light charging circuit, an ultrasonic charging circuit, a heat charging circuit, a heat harvesting circuit, or a circuit that harvests energy from the communication circuit. In some examples, the recharging circuit may recharge the rechargeable battery using power supplied from a replaceable battery (e.g., a battery supplied with a base component.)

The sensor electronics may also include one or more supercapacitors 284 in the sensor electronics package (as shown), or in the base. For example, the supercapacitor 284 may allow energy to be drawn from the battery in a highly consistent manner to extend a life of the battery. The battery may recharge the supercapacitor after the supercapacitor delivers energy to the communication circuit or to the processor, so that the supercapacitor is prepared for delivery of energy during a subsequent high-load period. In some examples, the supercapacitor may be configured in parallel with the battery. A device may be configured to preferentially draw energy from the supercapacitor, as opposed to the battery. In some examples, a supercapacitor may be configured to receive energy from the rechargeable battery for short-term storage and transfer energy to the rechargeable battery for long-term storage.

The supercapacitor may extend an operational life of the battery by reducing the strain on the battery during the high-load period. In some examples, a supercapacitor removes at least 10% of the strain off the battery during high-load events. In some examples, a supercapacitor removes at least 20% of the strain off the battery during high-load events. In some examples, supercapacitor removes at least 30% of the strain off the battery during high-load events. In some examples, a supercapacitor removes at least 50% of the strain off the battery during high-load events.

The sensor electronics 106 may also include a wireless communication circuit 218, which may for example include a wireless transceiver operatively coupled to an antenna. The wireless communication circuit 218 may be operatively coupled to the processor, and may be configured to wirelessly communicate with one or more peripheral devices or other medical devices, such as an insulin pump or smart insulin pen.

Peripheral device 250 may include, a user interface 252, a memory circuit 254, a processor 256, a wireless communication circuit 258, a sensor 260, or any combination thereof. The user interface 252 may, for example, include a touch-screen interface, a microphone (e.g., to receive voice commands), or a speaker, a vibration circuit, or any combination thereof, which may receive information from a user (e.g., glucose values) or deliver information to the user such as glucose values, glucose trends (e.g., an arrow, graph, or chart), or glucose alerts. The processor 256 may be configured to present information to a user, or receive input from a user, via the user interface 252. The processor 256 may also be configured to store and retrieve information, such as communication information (e.g., pairing information or data center access information), user information, sensor data or trends, or other information in the memory circuit 254. The wireless circuit communication circuit 258 may include a transceiver and antenna configured communicate via a wireless protocol, such as Bluetooth, MICS, or any of the other options discussed above. The sensor 260 may, for example, include an accelerometer, a temperature sensor, a location sensor, biometric sensor, or blood glucose sensor, blood pressure sensor, heart rate sensor, respiration sensor, or other physiologic sensor. The peripheral device 250 may, for example, be devices such as a hand-held smart device (e.g., smartphone or other device such as a proprietary handheld device available from Dexcom) 112, tablet 114, smart pen 116, watch 120 or other wearable device, or computer 118 shown in FIG. 1.

The peripheral device 250 may be configured to receive and display sensor information that may be transmitted by sensor electronics module 106 (e.g., in a customized data package that is transmitted to the display devices based on their respective preferences). Sensor information (e.g., blood glucose concentration level) or an alert or notification (e.g., "high glucose level", "low glucose level" or "fall rate alert" may be communicated via the user interface 252 (e.g., via visual display, sound, or vibration). In some examples, the peripheral device 250 may be configured to display or otherwise communicate the sensor information as it is communicated from the sensor electronics module (e.g., in a data package that is transmitted to respective display devices). For example, the peripheral device 250 may transmit data that has been processed (e.g., an estimated analyte concentration level that may be determined by processing raw sensor data), so that a device that receives the data may not be required to further process the data to determine usable information (such as the estimated analyte concentration level.) In other examples, the peripheral device 250 may process or interpret the received information (e.g., to declare an alert based on glucose values or a glucose trend. In various examples, the peripheral device 250 may receive information directly from sensor electronics 106, or over a network (e.g., via a cellular or Wi-Fi network that receives information from the sensor electronics or from a device that is communicatively coupled to the sensor electronics 106.)

Referring again to FIG. 2, the medical device 270 may include a user interface 272, a memory circuit 274, a processor 276, a wireless communication circuit 278, a sensor 280, a therapy circuit 282, or any combination thereof. The user interface 272 may, for example, include a touch-screen interface, a microphone, or a speaker, a vibration circuit, or any combination thereof, which may receive information from a user (e.g., glucose values, alert preferences, calibration coding) or deliver information to the user, such as e.g., glucose values, glucose trends (e.g., an arrow, graph, or chart), or glucose alerts. The processor 276 may be configured to present information to a user, or receive input from a user, via the user interface 272. The processor 276 may also be configured to store and retrieve information, such as communication information (e.g., pairing information or data center access information), user information, sensor data or trends, or other information in the memory circuit 274. The wireless circuit communication circuit 278 may include a transceiver and antenna configured communicate via a wireless protocol, such as Bluetooth, Medical Implant Communication System (MICS), Wi-Fi, Zigbee, or a cellular protocol (e.g., CDMA (Code Division Multiple Access) or GSM (Global System for Mobiles). The sensor 280 may, for example, include an accelerometer, a temperature sensor, a location sensor, biometric sensor, or blood glucose sensor, blood pressure sensor, heart rate sensor, respiration sensor, or other physiologic sensor. The medical device 270 may include two or more sensors (or memories or other components), even though only one is shown in the example in FIG. 2. In various examples, the medical device 270 may be a smart handheld glucose sensor (e.g., blood glucose meter), drug pump (e.g., insulin pump), or other physiologic sensor device, therapy device, or combination thereof. The medical device 270 may be the device 122 shown in FIG. 1.

In examples where the medical device 122 or medical device 270 is an insulin pump, the pump and analyte sensor system may be in two-way communication (e.g., so the pump can request a change to an analyte transmission protocol, e.g., request a data point or request data on a more frequency schedule, and the analyte sensor system provides the requested data accordingly), or the pump and analyte sensor system may communicate using one-way communication (e.g., the pump may receive analyte concentration level information from the analyte sensor system, for example, not in response to a request. In one-way communication, a glucose value may be incorporated in an advertisement message, which may be encrypted with a previously-shared key. In a two-way communication, a pump may request a value, which the analyte system may share, or obtain and share, in response to the request from the pump, and any or all of these communications may be encrypted using one or more previously-shared keys. An insulin pump to may receive and track analyte (e.g., glucose) values transmitted from analyte sensor system 102 using one-way communication to the pump for one or more of a variety of reasons. For example, an insulin pump may suspend or activate insulin administration based on a glucose value being below or above a threshold value.

In some examples, the system 100 shown in FIG. 1 may include two or more peripheral devices that each receive information directly or indirectly from the analyte sensor system 102. Because different display devices provide may different user interfaces, the content of the data packages (e.g., amount, format, and/or type of data to be displayed, alarms, and the like) may be customized (e.g., programmed differently by the manufacture and/or by an end user) for each particular device. For example, in the embodiment of FIG. 1, a plurality of different peripheral devices may be in direct wireless communication with a sensor electronics module (e.g., such as an on-skin sensor electronics module 106 that is physically connected to the continuous analyte sensor 104) during a sensor session to enable a plurality of different types and/or levels of display and/or functionality associated with the displayable sensor information, or, to save battery power in the sensor system 102, one or more specified devices may communicate with the analyte sensor system and relay (i.e., share) information to other devices directly or through a server system (e.g., network-connected data center) 126.

Example Methods

Figure 3:
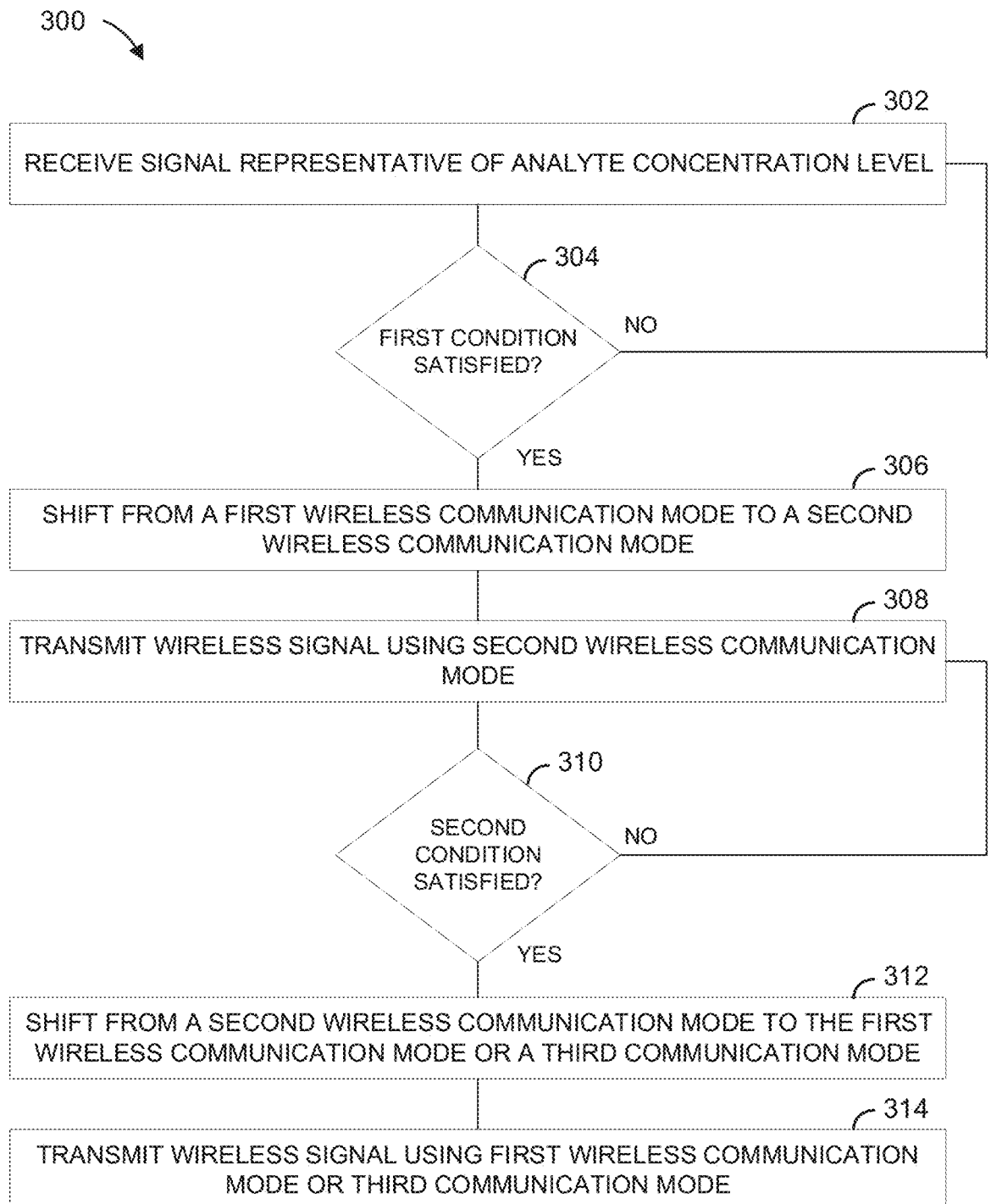
FIG. 3 is a flowchart illustration of an example method of managing power consumption in an analyte monitoring system.

FIG. 3 is a flowchart illustration of an example method 300 of managing power consumption in an analyte monitoring system. The method may, for example, include modulating power output from a first communication circuit to increase range or bandwidth by increasing power output and to conserve energy by decreasing power output from the first communication circuit. The method may, for example, be implemented in a system as shown in FIG. 1 or a device as shown in FIG. 2. The method may be repeated continuously or recurrently (e.g. periodically) or responsive to one or more events to manage power on an ongoing basis.

At 302, a signal representative of an analyte (e.g., glucose) concentration level may be received. The signal may be received, for example, from an analyte sensor, which may, for example, be a portion of a continuous glucose monitoring system as described above.

At 304, a determination is made as to whether a first condition is satisfied. In some examples, a processor operatively coupled to an analyte sensor (e.g., CGM processor) may determine whether the first condition is satisfied. In some examples, a processor in a peripheral device (e.g., smart phone or other display device) may determine whether the first condition is satisfied. Responsive to the condition not being satisfied, the method may return to step 302 and continue to receive analyte concentration levels.

In some examples, the first condition may be a connectivity condition, and step 304 may include determining whether the connectivity condition has been satisfied. The connectivity condition may, for example, include the existence of a connection (e.g. Bluetooth connection), a reliability of a connection (e.g., based upon the occurrence of successful connection attempts, or based on connection failures), or a quality of the connection based on one or more signal strength measurement parameters (e.g., a received signal strength indicator (RSSI.)) Determining whether the first condition is satisfied may include applying a connectivity parameter to a model. The model may include a plurality of communication states. The communication states may, for example, be based upon reliability of communication, elapsed time with consecutive successful communication sessions, elapsed time since an unsuccessful attempt (or series of attempts) to establish communication, or other measures of communication effectiveness or reliability.

The first condition may additionally or alternatively include an analyte management condition, such as a range (e.g., a glucose value range) or a trend (e.g. one or more analyte (glucose) levels being above or below a specified value or within a specified range, or a rate of change of analyte concentration levels being above or below a rate-of-change threshold.) In various examples, determining whether the first condition is satisfied may include analyzing the analyte signal, or an analyte parameter based on the analyte signal, to determine whether the analyte management condition is satisfied.

In some examples, determining whether a first condition is satisfied may, for example, include applying an analyte parameter to a model (e.g., a state model). In some examples, the condition may correspond to recognition of a state of disease management that is clinically relevant to the user of a peripheral device. A condition may, for example, be based upon by an analyte level (e.g. low estimated glucose level or high estimated glucose level), a trend (e.g., analyte concentration level rate of change or a predictive data), a deviation from a trend (e.g., reversal of a trend), or a probability of a clinically relevant condition occurring in the future (e.g., urgent low glucose soon).

In some examples, a condition may correspond to or be based upon one or more requirements of a peripheral device, such as an insulin pump. For example, a connectivity state may go from a low power usage model to a high power usage model based upon a basal or bolus insulin deliver conditions (e.g., a high power usage model or more reliable or frequency communication may be used when insulin is being delivered to avoid loss of a connection.)

In some examples, a state model may include a plurality of analyte concentration level states. An analyte concentration level state may be defined or determined by an analyte concentration range or trend (e.g., glucose below target range, glucose in target range, or glucose above target range.)

In some examples, a state model may additionally or alternatively include a plurality of communication states (e.g., low power state, high power state or high-reliability state, partnered state to coordinate with a peripheral device such as a pump, battery life extension state to assure that predicted battery life meets a battery life criterion.)

Responsive to the condition being satisfied, the method 300 may include, at 306, shifting from a first wireless communication mode to a second wireless communication mode responsive to satisfaction of a condition. In some examples, shifting from the first wireless communication mode to the second wireless communication mode includes reducing power output from a communication circuit to save energy. In some examples, the first wireless communication mode may consume more power than the second wireless communication mode. This shift to the second wireless communication mode may allow an analyte monitoring system to save power when the first condition is satisfied by shifting to the second wireless communication mode. In some examples, a system may balance need for communication and power consumption. For example, satisfaction of the first condition may be associated with a less urgent need for communication (e.g., a determination that analyte concentration levels and/or trends are in a "managed" range or state), in which case less frequent (e.g. on 15-minute intervals instead of 5-minute intervals), less power-demanding (e.g. lower transmit power or lower power protocol), or less automatic or on-demand communication (e.g. NFC instead of Bluetooth) communication may be acceptable. In some examples, a processor may monitor power consumption continuously or recurrently intermittently or may increase or decrease power consumption responsive to a protocol or satisfaction of a condition.

In some examples, the second wireless communication mode uses less power than the first wireless communication mode. In some examples, the first wireless communication mode may be a continuous connection mode as defined by a connection protocol (e.g., Bluetooth) and the second wireless communication mode may be a periodic connection mode. The periodic connection mode may require fewer wireless transmissions required to maintain an active state (e.g. based on a minimum connection interval) than the continuous connection mode. In some examples, the first wireless communication mode may be a two-way communication mode and the second wireless communication mode may be a one-way communication mode that includes data transmission from the first communication circuit. For example, the one-way communication mode may be a broadcast mode (e.g., in a Bluetooth protocol.) The one-way communication protocol may require less time actively transmitting and receiving, and therefore uses less power.

In some examples, the first wireless communication mode has a longer range than the second wireless communication mode. For example, the first communication mode may include a medium to long range wireless communication method or technology (e.g. Bluetooth or MICS communication), and the second communication mode may use a short range wireless method or technology (e.g. NFC or inductive communication). Bluetooth tends to have a relatively long range (e.g., up to 100 m). MICS also tends to have a relatively long range (e.g., up to about 6 m), but the MICS range is usually shorter than Bluetooth. NFC and other inductive communication techniques tend to have a relatively short range (e.g., 4 cm up to about 30 cm), but require less power, no power, and in some examples can harvest power.

In some examples, an authentication process may be performed in the first communication mode (e.g., in a two-way communication scheme to allow for exchange of keys), and the system may shift to the second communication mode after authentication. In some examples, the system may transmit encrypted broadcast data via the second wireless communication mode. The encrypted broadcast data may, for example, include analyte concentration level information, trend information, or state information. In some examples, the encrypted broadcast data may be used to determine whether to shift from the second wireless communication mode to the first wireless communication mode (e.g., to determine whether the second condition is satisfied.) In some examples, the encrypted broadcast data may include an indication to shift back from the second wireless communication mode to the first wireless communication mode. For example, an analyte system processor (e.g., CGM processor) may apply an algorithm to determine whether to shift back to the first mode (e.g., back to two-way communication), and the peripheral device may transmit a bit flag in the broadcast packet. In some examples, a peripheral device (e.g., smart phone or other handheld display device) may apply an algorithm to determine whether to shift from the first mode to the second mode (e.g., to save power.)

After shifting to the second wireless communication mode, the method may include at 308 transmitting using the second wireless communication mode for a period of time, or until the satisfaction of a second condition (e.g., as determined at step 310.)

At 310, the method may include determining whether a second condition is satisfied. The second condition may be a different condition, or may be an inverse of the first condition (e.g., an analyte level or trend moving out of range or otherwise satisfying or failing to satisfy a glucose management condition, or failure to satisfy a communication condition.) When the second condition is not satisfied, the method may return to transmitting the wireless signal using the second (e.g., low-power) wireless communication mode at 308.

Responsive to the second condition being satisfied, the method may include ceasing to use the second wireless communication mode. For example, when the second condition is satisfied, the method may include, at 312, shifting from a second wireless communication mode to the first wireless communication mode. In some examples, the method 300 may include shifting from the second communication mode back to the first communication mode includes increasing power output to increase communication range or bandwidth, and, at 314, communicating using the first wireless communication mode. Alternatively, the method may at 310 include shifting to a third wireless communication mode (e.g., to an intermediate power-consuming mode (e.g., intermittent two-way communication), or to a high-priority communication mode (e.g., continuous connection) that may consume more power than the first mode) and communicating using the third wireless communication mode at 314.

In some examples, the method 300 may include shifting from a one-way communication mode (e.g., broadcast) to a two-way communication mode when a sensor calibration is needed or to acknowledge that an alert or alarm has been received.

Figure 4:
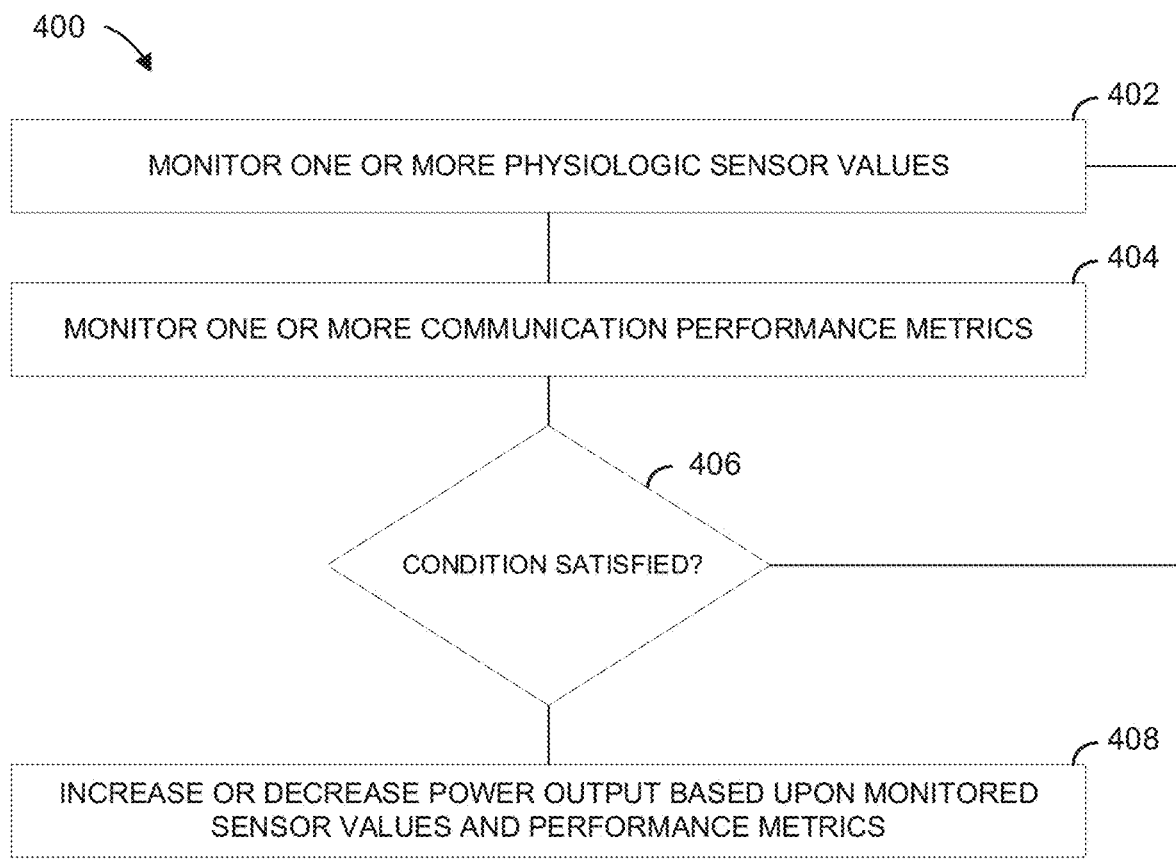
FIG. 4 is a flowchart illustration of an example method of managing power output based upon monitored sensor values or performance metrics.

FIG. 4 is a flowchart illustration of an example method 400 of managing power output based upon monitored sensor values or performance metrics. The method may be implemented, for example, in a system as shown in FIG. 1 or a device as shown in FIG. 2.

The method 400 may include, at 402, monitoring one or more physiologic sensor values (e.g., analyte concentration level, temperature, activity level, heart rate). The physiologic sensor values may, for example, be received from a wearable sensor device that includes an analyte sensor (e.g., analyte sensor) and a communication circuit. The wearable sensor device may, for example, includes an analyte monitor, and the one or more physiologic sensor values include an estimated analyte concentration level.

The method may also include, at 404, monitoring one or more communication performance metrics pertaining to communication to or from the wearable sensor device. The communication performance metrics may, for example, include packet capture rates or received signal strength indicator values.

The method may further include, at 406, determining whether a condition is satisfied. The determination may, for example, be based at least in part upon the monitored physiologic sensor values (e.g., satisfaction of an analyte management condition) or the communication performance metrics (e.g., satisfaction of a communication reliability condition), or both or a combination thereof. For example, the method may include determining whether an analyte management condition is satisfied based at least in part on the estimated analyte concentration level. The analyte risk management condition may, for example, include a range, a trend, a projected analyte level, or other analyte management information. As described in detail above, the condition may correspond to recognition of a state of disease management that is clinically relevant to a user of a peripheral device The method may additionally or alternatively include determining whether a communication reliability condition is satisfied based at least in part on the communication performance metrics, and responsive to determining that the communication reliability condition is satisfied, conserving power by shifting to a more energy efficient communication scheme, or maintaining a current communication scheme (e.g., refraining from increasing power output). The communication reliability condition may, for example, be based on signal strength or packet rate falling below a threshold, or a combination thereof.

In some examples, the system may maintain the status quo (e.g., make no change) when a condition is satisfied. In some examples, a condition may be a negative condition, e.g., a negative condition may be satisfied when some combination of requirements is not met.

Responsive to the satisfaction of a condition, the method may further include, at 408, increasing or decreasing power output of the communication circuit. In some examples, the method may include shifting to a lower-power protocol. For example, the method may include shifting from a long-range communication protocol to a short range communication protocol (e.g., MICS or Bluetooth to NFC), or from a continuously connected mode to a recurrently (e.g., periodically) connected mode, or from a two-way communication protocol to a one-way communication mode (e.g., broadcast mode.) In some examples, the method may include changing one or more communication parameters (e.g., shifting the communication mode). In some examples, the method may include periodically communicating the estimated analyte concentration level to another device, and increasing or decreasing power output may include decreasing a frequency of communication of the estimated analyte concentration level.

In some example, increasing or decreasing power output may include shifting a frequency, shifting a mode, shifting a power level, or shifting a time period between communications, to increase communication range or reliability, or to conserve energy. For example, a system may shift between communicating one or more of once a minute, once every five minutes, once every ten minutes, or once every 30 minutes.

In some examples, increasing or decreasing power output may include restricting communication to a specified peripheral device of a plurality of available peripheral devices (e.g., increasing power to a pump but not to a smart watch). In some examples, the method may further include determining a specified peripheral device based on a schedule, a priority scheme, or a location. In some examples, the method may further include determining a battery status, wherein a communication scheme is modified based at least in part on the monitored physiologic sensor values, the communication performance metrics, and the battery status.

Figure 5:
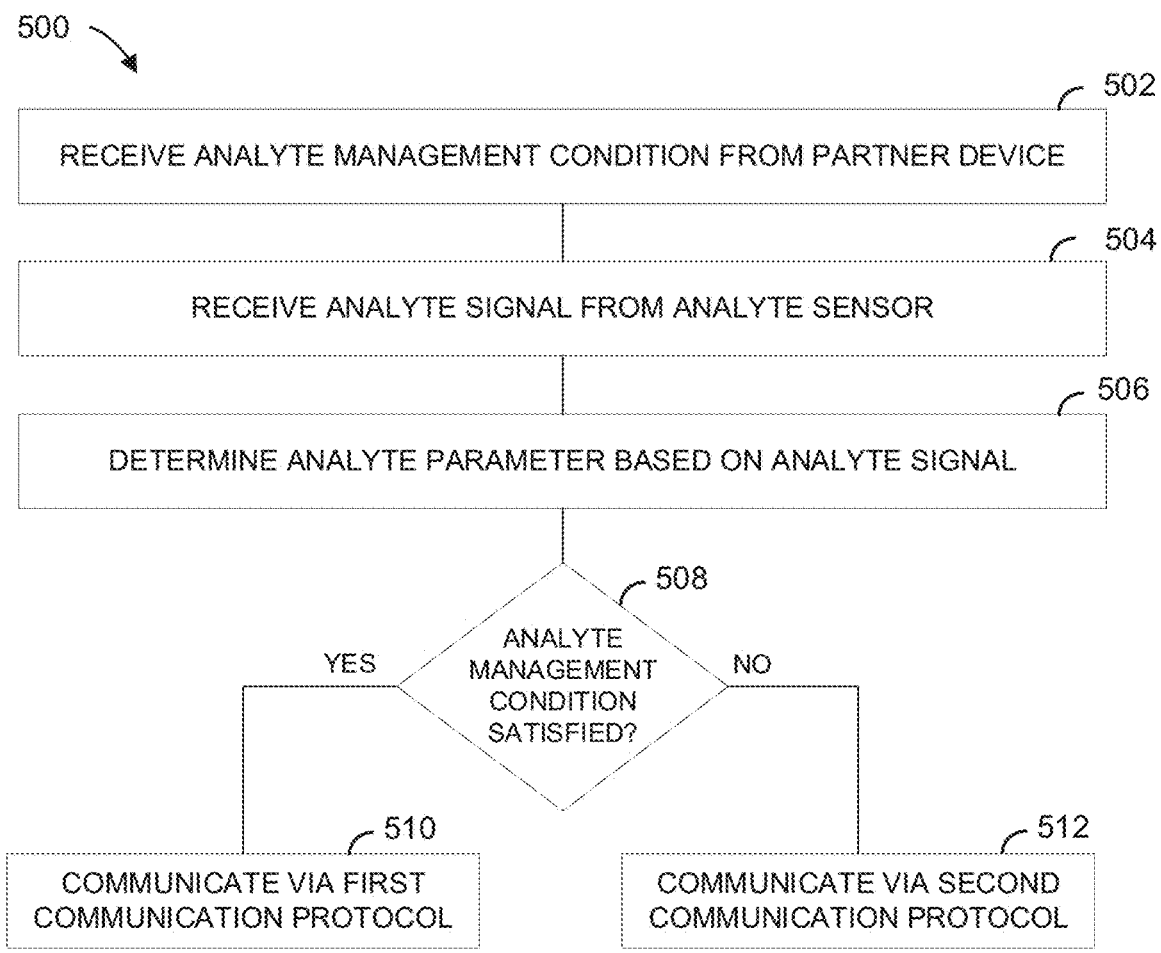
FIG. 5 is a flowchart illustration of an example method of selecting a communication protocol based upon satisfaction of an analyte management condition.

FIG. 5 is a flowchart illustration of an example method 500 of selecting a communication protocol based upon satisfaction of an analyte management condition. The method 500 may, for example, be applied to an analyte monitoring system including a communication circuit and an analyte sensor configured to generate a signal representative of an analyte concentration level, a processor configured to control operation of the system, and a battery configured to power the system. The method may be implemented, for example, in a system as shown in FIG. 1 or a device as shown in FIG. 2.

The method may include, at 502, receiving an analyte management condition from a partner device, such as an insulin pump or an insulin pen. The analyte management condition may include, for example, a range of analyte concentration levels (e.g., glucose concentration levels), a rate or change, or other parameter based on one or more analyte concentration levels. In various examples, the analyte management condition may be determined by the partner device, or may be input by a user of the partner device.

At 504, the method 500 may further include receiving, e.g., from an analyte sensor, an analyte signal representative of an analyte concentration level (e.g., glucose concentration level.) The method 500 may also include, at 506, determining an analyte parameter based at least in part upon the analyte signal. For example, an estimated analyte concentration level (e.g., estimated glucose concentration level) may be determined. The method 500 may further include, at 508, determining a whether the analyte management condition is satisfied. The determination may be based at least in part on the analyte parameter. For example, the method may include determining whether an estimated analyte concentration level falls below a threshold, or exceeds a threshold, or a rate of change exceeds a rate of change threshold, or a predicted analyte concentration level meets a condition (e.g., above or below a threshold.) In some examples, determining whether the analyte management condition is satisfied may include applying the analyte parameter to a model (e.g., state model). The model may be predefined or may be learned from data, and may reside in the system (e.g., in the sensor electronics) or locally (e.g., on a smart device on or near the patient (host), or may reside on a remote system (e.g., on a networked resource.) One or more parameters (e.g., an analyte parameter) may be applied to the model (e.g., provided as input) and a state may be determined by applying the one or more parameters to the model. The state may, for example, relate to the host, such as a glucose state (e.g., in range, out of range, or trend) or may relate to communications (e.g., reliable or unreliable), or a combination thereof.

The method 500 may further include determining a communication protocol for communicating with the partner device based at least in part on whether the analyte management condition is satisfied. For example, the method may include, at 510 communicating via a first communication mode (e.g., power level, frequency, protocol) when the condition is satisfied, and, at 512, communicating via second communication mode when the condition is not satisfied. In an example, when an estimated analyte level (e.g., estimated glucose level) falls within a safe zone (e.g., 80 to 140 mg/DL), which may be specified by a partner device (e.g., insulin pump) or based upon a requirement or characteristic of the partner device, an analyte monitor (e.g., CGM) may communicate (e.g., advertise in a Bluetooth protocol) less frequently (e.g., every 15 or 30 minutes instead of continuously or every 1 or 5 minutes) to conserve power, or may shift to a one-way communication scheme, or may otherwise control operation of the system conserve power as described herein.

Figure 6:
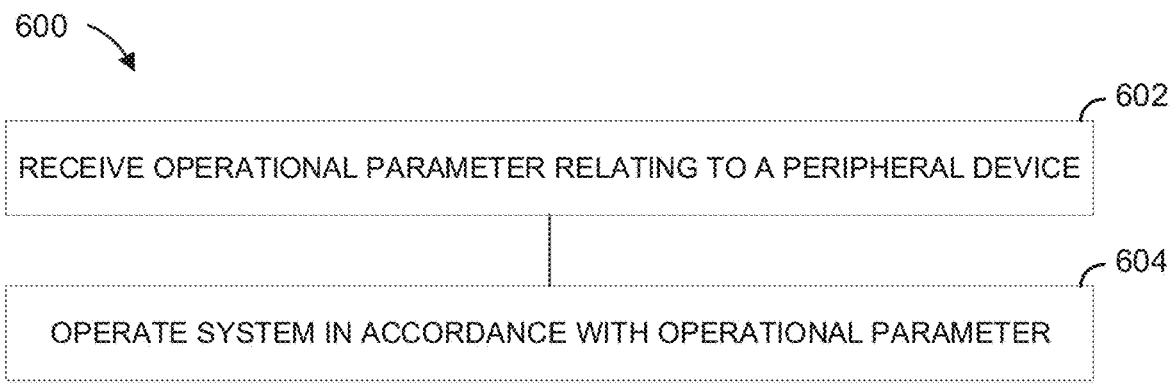
FIG. 6 is a flowchart illustration of an example method of managing power using an operational parameter received from a peripheral device.

FIG. 6 is a flowchart illustration of an example method 600 of managing power using an operational parameter received from a peripheral device. The method 600 may be implemented in an analyte monitoring system (e.g., CGM) including a communication circuit, an analyte sensor configured to generate a signal representative of an analyte concentration level, a processor configured to control operation of the system, and a battery configured to power the system. The method may, for example, be implemented in a system as shown in FIG. 1 or a device as shown in FIG. 2.

The method 600 may include, at 602, receiving via the communication circuit an operational parameter relating to a peripheral device. The peripheral device may, for example, include a drug pump, a smart pen, a handheld device (e.g., smart phone) or another type of display device that is configured to communicate with the analyte monitoring system. The operational parameter may be received from the peripheral device, or the operational parameter may be received from a remote resource (e.g., a server) or local device (e.g., smartphone app). In some examples, the operational parameter may be retrieved from a memory circuit based upon an identity or characteristic of the peripheral device (e.g., retrieved from a lookup table.) In an example, a system may communicate with a peripheral device and receive (or exchange) device identification information, and the system may then provide the device identification information (e.g., via a device such as a smart phone) and receive the operational parameter, which may be received from or determined by a remote resource (e.g., network server) or by a smart device.

In various examples, the operational parameter may, for example, include a battery management parameter, a calibration schedule parameter, a sensor accuracy parameter, or contextual information. In some examples, the operational parameter may include contextual information from the peripheral device (e.g., information about an interaction of the peripheral device with another device or a network environment.) For example, the operational parameter may include information about a connection state of the peripheral device (e.g., a network or remote server ("cloud") connection, RSSI, or a missed communication). In some examples, the operational parameter may include a status of the peripheral device, such as a battery level, an activity level (e.g., determined using an accelerometer on the peripheral device), location (e.g., GPS or based on network connection status or strength), display status (e.g., on or off), alert state (e.g., alert active or not active), alert acknowledged (e.g., input received from user to acknowledge receipt of alert), use mode (e.g., open loop or closed loop), or status of a pending event or action (e.g., waiting for an action or event.)

The method may further include, at 604, operating a system (e.g., analyte monitoring system such as a CGM) based at least in part upon the operational parameter. In various examples, a determination may be made based on the operational parameter, the system may be operated based at least in part on the determination. For example, the system may determine whether the operational parameter is within acceptable bounds. In some examples, the system may, for example, determine whether an analyte concentration is a defined analyte concentration range or satisfies a trend criterion, such as an average rate of change being below a threshold value.

In some examples, the operational parameter may include an operational requirement of the peripheral device. The method 600 may include controlling operation of the system to satisfy the operational requirement.

In an example, the operational requirement may include a sensor accuracy requirement and the system may be controlled to satisfy the sensor accuracy requirement (e.g., calibrate or replace a sensor that does not satisfy the sensor accuracy requirement). In an example, the operational requirement may include a calibration schedule, and the system may be operated to satisfy the calibration schedule (e.g., a system may prompt a user for calibrations to satisfy the schedule received from a partner device).

In an example, the operational requirement may include a battery life requirement, and the system may be operated to satisfy the battery life requirement (e.g., the system may suggest replacement of a battery, or a transceiver or other component that contains a battery, to assure that the battery life requirement is satisfied). In some examples, the operational parameter may include a specified period of time (e.g., a pump session time), and operation of a system (e.g., continuous analyte sensor) may be controlled to manage energy consumption from the battery (e.g., analyte sensor battery) so that energy stored in the battery is not depleted before the specified period of time expires, e.g., the processor may control operation of the communication circuit in a manner calculated to assure that energy stored in the battery is not depleted before the specified period of time expires. For example, the processor may modify a communication scheme to conserve battery energy during the specified period of time. For example, the processor may shift to a communication mode that consumes less energy (e.g., shift from MICS or Bluetooth to NFC, shift from an always connected mode to a recurrent (e.g., periodic) communication mode, or shift from a two-way communication mode to a one-way (e.g., broadcast) communication mode.

In some examples, a system (e.g., analyte monitoring system) may be configured to communicate with a second device (e.g., in addition to a peripheral device such as a pump or smart pen), and the method may include restricting communication by the communication circuit so that the system communicates only with the peripheral device during the specified period of time. For example, the system may receive a whitelist (e.g., from the peripheral device or from a smart device or network resource) that the system may use during the specified period of time. In another example, the system (e.g., analyte monitoring system) may receive an operational parameter that indicates that the system may only communicate with the peripheral device during a specified period of time (e.g., the parameter may prescribe a communication schedule to reduce a need to broadcast). In another example, the system (e.g., analyte monitoring system) may receive an operational parameter that indicates that the system may communicate only with the peripheral device (e.g., with no other devices) during a specified period of time (e.g., to assure that a communication to a pump is successful). In another example, the system may receive an operational parameter to blacklist a communication device, such as a device that was previously connected with the system (e.g., a previous pump that was replaced may be blacklisted.)

In some examples, the operational parameter may include a specified number of additional peripheral devices, and the method may include communicating only with the peripheral device and the specified number of additional devices, wherein excessive consumption of energy stored in the battery is avoided by limiting the number of devices with which the analyte monitoring system communicates.

In some examples, the operational parameter may include an identification of one or more additional peripheral devices, and the method may include communicating only with the identified one or more additional devices, wherein excessive consumption of energy stored in the battery is avoided by limiting the number of devices with which the analyte monitoring system communicates. For example, an analyte monitoring system may communicate with a default or user-specified primary device. In some examples, the identification may specify a specific device, e.g., using a device ID. In some examples, the identification may specify a type of device (e.g. a watch). Types of peripheral devices may include, for example, a handheld device (e.g., smartphone), a watch, a tablet, a pen, a pump, or a desktop computer.

In some examples, a system (e.g., analyte monitoring system) may receive information about connections between peripheral devices. For example, an analyte system may receive information that a smart phone is in communication with a watch. Responsive to receiving information that a first peripheral device is in communication with a second peripheral device, the system may restrict communication to a specified device or group of devices (e.g., an analyte monitoring system may communicate with a smart phone, or smartphone and pump) and rely on the specified device to communicate with a third device (e.g., the smartphone may pass information to a smartwatch to reduce battery consumption by an analyte sensor system.)

In some examples, an operational parameter may be a schedule for providing information such as an analyte level or trend (or both), and a system may communicate according to the schedule. For example, an analyte signal representative of an analyte concentration level may be received from an analyte sensor, processed to determine an estimated analyte concentration level, and transmitted via a wireless signal (e.g., using a communication circuit) according to a schedule specified by the operational parameter.

In some examples, a system (e.g., analyte monitoring system) may receive an identification (e.g., list) of one or more authorized peripheral devices. The system may accept operational parameters or communication requests from one or more peripheral devices based upon the identification of authorized devices.

Figure 7A:
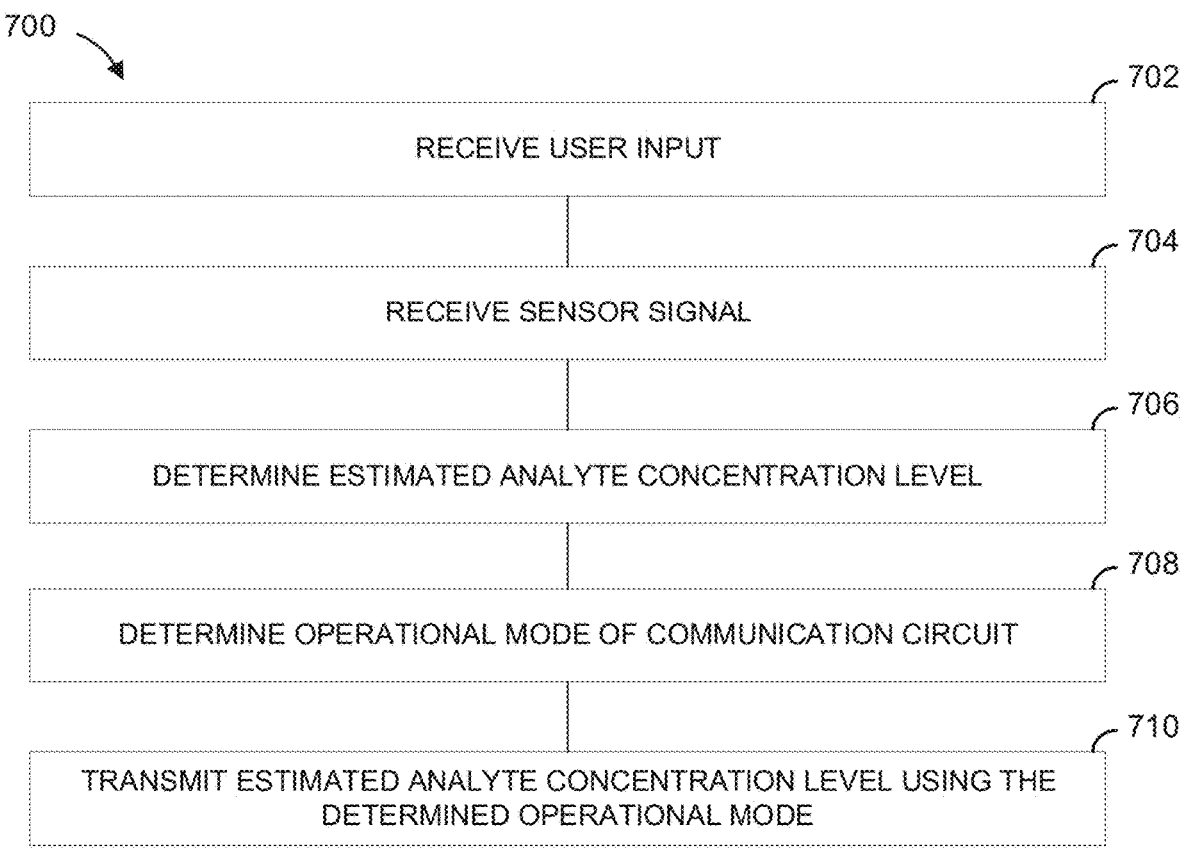
FIG. 7A is a flowchart illustration of an example method of managing power based upon user input.

FIG. 7A is a flowchart illustration of an example method 700 of managing power based upon user input. In some examples, the method 700 may be implemented in a system that may include an analyte sensor configured to generation a signal indicative of an analyte concentration level in a host, a processor configured to determine an estimated analyte concentration level based on the signal, a communication circuit configured to transmit the estimated analyte concentration level or information based on the estimated analyte concentration level via a transmitted communication signal, and to receive user input via a detected communication signal. The system may be configured to control a mode of communication for the communication circuit based at least in part on the user input. The system may, for example, be the system 200 shown in FIG. 2.

At 702, user input is received. The user input may be received directly, e.g., via a user interface (e.g., a graphical user interface GUI) or may be received from another device (e.g., a smart phone or other smart device) that may receive the user input via a user interface. In one example, the user interface may include menus and buttons (e.g., providing various options as described below), and the user may provide inputs via selecting the options from the menu and pressing the buttons. In some examples, the user input may be received over a network. For example, a host (e.g., child) to which an analyte sensor (e.g., glucose sensor) is attached may be in a first location, and the user (e.g., a caregiver) may provide the user input at a second location (e.g., via a smart phone) and the input may be relayed over a network (e.g., cellular network or the internet) to a smart device that is near the host.

The user input may, for example, include a request to initiate an energy-saving mode. The user input may also relate to energy management, e.g., the user input may include a request to align an estimated battery life with a parameter of a partner device (e.g., a pump session.) In some examples, the user input may include a specified condition. In some examples, responsive to satisfaction of the specified condition, the system may communicate less frequently or take other steps to consume less energy. In other examples, the system may enter a low-power consumption mode, and over-ride the low-power consumption mode responsive to satisfaction of the specified condition (e.g., estimated glucose level moving out of a safe range, or initiation of delivery of basal or bolus insulin by a pump.)

At 704, a sensor signal may be received from an analyte sensor. The sensor signal may, for example, be indicative of an analyte concentration level in a host (e.g., indicative of a glucose concentration.) The sensor signal may be received, for example, by a processor 204 as shown in FIG. 2 from an analyte sensor 104.

At 706, an estimated analyte concentration level (e.g., estimated glucose concentration level) is determined based on the sensor signal.

At 708, an operational mode of the communication circuit may be determined based at least in part on the user input. The determined operational mode may, for example, be an energy-saving mode, in which power consumption by the communication circuit or by the system may be reduced. The system may invoke any of the methods described herein to conserve or manage energy expenditure (e.g., the system may communicate less frequently than in a normal mode of operation, or limit the number of devices with which the system communicates, or communicate using a low-power technique (e.g., NFC) for non-critical communications or for all communications or for all communications.)

At 710, the estimated analyte concentration level, or information based on the estimated analyte concentration level, may be transmitted via the communication circuit using the determined operational mode. Transmitting using the energy-saving mode include, for example, transmitting information less often than in a normal operating mode, or transmitting using a less power-intensive mode of communication (e.g., NFC as opposed to Bluetooth), or communicating with fewer devices (e.g., communicating with a pump but not a watch), or communication via a peripheral device (e.g., communicating with a watch through a smartphone.

In some examples, a communication circuit may be controlled based at least in part on the analyte concentration level.

In some examples, a system (e.g., CGM system) may determine whether a condition is satisfied based at least in part on the analyte concentration level and control operation of the communication circuit to decreasing power consumption by the communication circuit based upon the determination of whether the condition is satisfied. For example, the condition may include range of analyte concentration levels, and determining whether the condition is satisfied may include determining whether the determined analyte concentration level falls within the range of analyte concentration levels. In an example, when an analyte concentration level is well controlled (e.g., estimated glucose level between 80 and 150 mg/dL and steady (e.g., no rapid rate of change)), a system may communicate less frequently that when an analyte concentration level is not well controlled (e.g., estimated glucose level beyond a specified threshold, e.g., below 70 mg/DL or over 150 mg/dL or 200 mg/DL or 250 mg/DL, or rising or falling quickly or a combination thereof.)

In some examples, the condition may include a trend condition, and determining whether the condition is satisfied may include determining whether the trend condition is satisfied using a plurality of analyte concentration levels. For example, a trend condition may include an analyte concentration level rate of change being below a specified threshold (e.g., estimated glucose rate of change not more than 2 mg/dL/minute or not more than 3 mg/dL/minute). The trend condition may also include an analyte concentration level (e.g., estimated glucose concentration level rate of change not more than 2 mg/dL per minute when the estimated glucose concentration level is less than 120 mg/dL.

In some examples, transmitting using the determined operational mode may include decreasing power consumption by refraining from automatic transmission of analyte concentration information, or transmitting analyte concentration information less often. In some examples, transmitting using the determined operational mode may include transmitting only in response to a request (e.g., shift to a "pull" mode instead of "push" mode), or transmitting less often unless a request is received (e.g., a request from a partner device or a user.)

In some examples, a determined operational mode may be overridden to communicate responsive to an analyte concentration level falling below a threshold or outside a range.

In some examples, the user input may include a specification of a condition, and the operation of the communication circuit may be modified responsive to satisfaction of the condition. The condition may, for example, includes a range of analyte concentration levels or an analyte trend condition, or any other condition discussed herein.

In some examples, a patient state may be determined based upon one or more analyte concentration levels, and operation of the communication circuit may be modified to reduce power consumption responsive to the patient state satisfying a safety condition. For example, a patient state may be determined by applying one or more analyte concentration levels to a model, such as a state model that may include one or more states determined by the model responsive to analyte concentrations level(s), and optionally also determined by contextual factors or information about the device (e.g., battery level) or an information about partner device (e.g., a pump.)

In some examples, the user input may include a request to operate the system in a manner to assure that an estimated battery life matches or exceeds an operation parameter relating to a partner device. For example, the operational parameter may be a period of time (e.g., a pump session time), and the system may operate the in a manner to extend the life of a battery in the system so that the battery does not expire (e.g., be depleted to a charge level that is insufficient to perform a function) before the period of time expires.)

In some examples, the system may monitor for an alert condition based at least in part upon the estimated analyte concentration level and the system may override the energy savings mode to communicate an alert.

In some examples, a determined operational mode of communication may include a hibernation mode (e.g., low-power consumption mode). In the hibernation mode, a system may stop communication, or may communicate only very infrequently, or may only list but not transmit, or transmit very unfrequently, or one or more non-communication operations (e.g., sensing) may be suspended, or any combination thereof. In some examples, a system may enter a hibernation mode responsive to a user input that includes a request to stop a sensor session, or responsive to a request to start a sensor session (e.g., because after starting a session a sensor may not be used during a warm-up period in which the host/sensor adapts to the insertion of a sensor into the host). In some examples, the system may shift out of the hibernation mode after a specified period of time (e.g., after expiration of a warm-up period.)

Figure 7B:
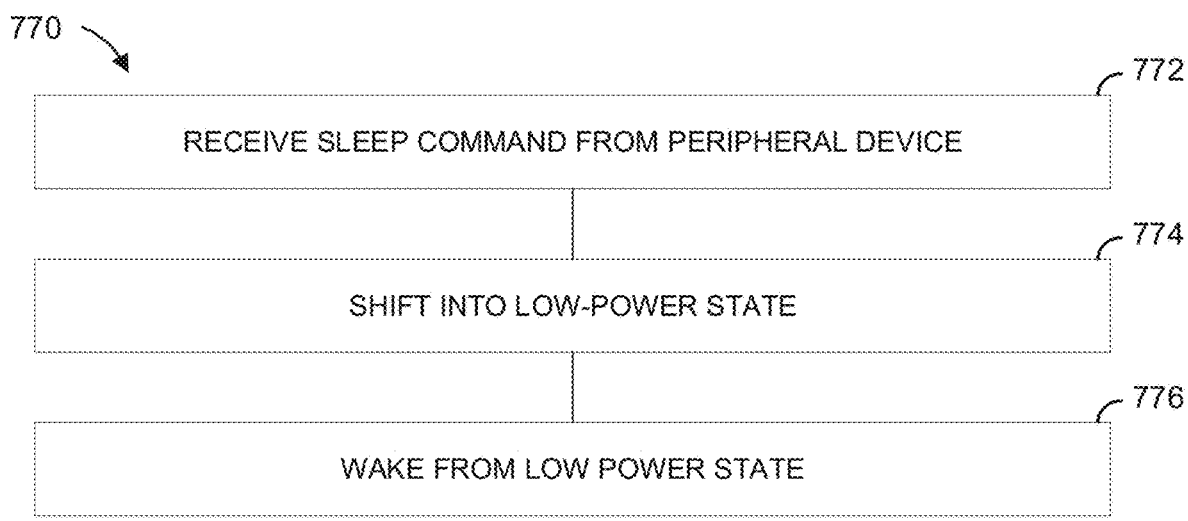
FIG. 7B is a flowchart illustration of an example method of managing power based upon a sleep command.

FIG. 7B is a flowchart illustration of an example method 770 of managing power based upon a sleep command (e.g., an instruction to enter a hibernation mode or other low-power consumption state). The method may be applied, for example, to an analyte monitoring system including a communication circuit and an analyte sensor configured to generate a signal representative of an analyte concentration level, a processor configured to control operation of the system, and a battery configured to power the system. The method may be implemented, for example, in a system as shown in FIG. 1 or a device as shown in FIG. 2.

The method 770 may include, at 772, receiving via the communication circuit a sleep command from a peripheral device. It may be desirable, for example, to cause an analyte monitoring system to sleep during a warm up period (e.g., after application of a sensor to a host, a warm-up period may be required before sensor readings begin.) The method 770 may include, at 774, shifting the system into a low-power state responsive to receipt of the sleep command. In some examples, the system may stop communicating in a sleep state. For example, a communication circuits may stop sending and receiving completely for a period of time, or the communication circuit may enter a listening-only mode, which may optionally involve a lower-power listening mode than normal operation (e.g., longer duty cycles or wake up and listen on a schedule.) In some examples, other portions of a system may also stop consuming energy or enter a low-power mode. For example, analyte sensor may stop applying a sensing voltage to an electrode or a processor may stop collecting or processing data. In another example, when the system is in the low power mode, the analyte sensor may still continue to apply voltage for analyte measurement purposes, however, the transmission/communication circuit may remain in the sleep or low power mode. Yet, in another example, when sensor electronics are removed from a host (e.g., when a transmitter is disconnected from a sensor), the sensor electronics may stop processing or communicating (e.g., because the sensor electronics are not receiving sensor data anyway.)

The method may include, at 776, waking the system from the low power state. In some examples, the system may include a clock that triggers a wakeup event when a period of time (e.g., warm-up period) expires, e.g., using a timer or at a specified time. In some examples, the method may include waking the analyte monitoring system in response to a wake-up command, e.g., in response to a command from a peripheral device such as a pump or a smart device (e.g., smart phone or proprietary hand-held device).

Figure 8:
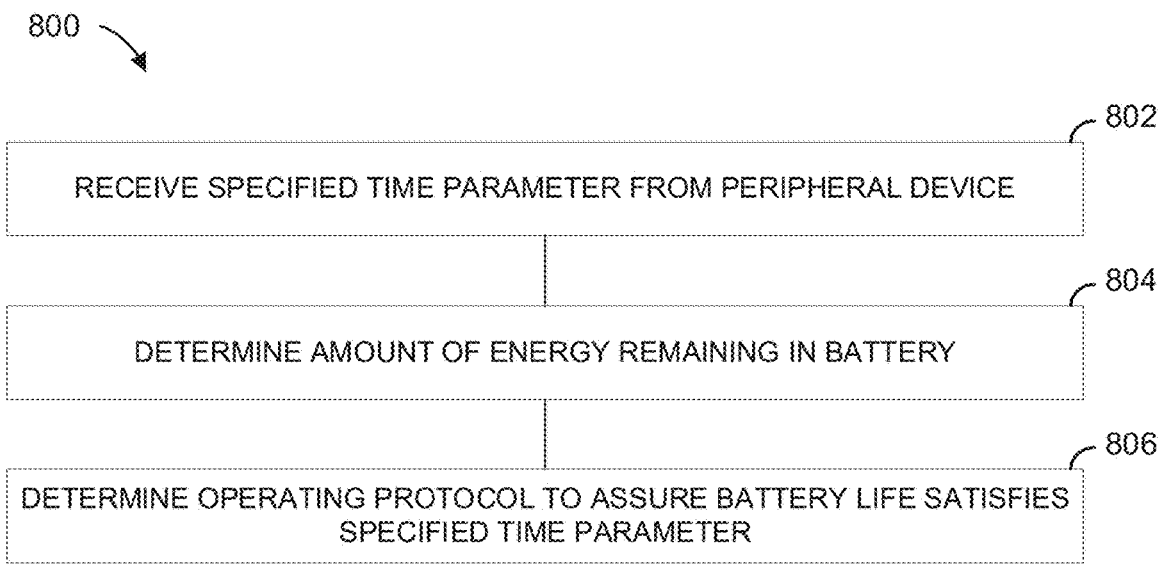
FIG. 8 is a flowchart illustration of an example method of determining an operating protocol to assure battery life satisfies a specified time parameter.

FIG. 8 is a flowchart illustration of an example method 800 of determining an operating protocol to assure battery life satisfies a specified time parameter. The method may be applied, for example, to an analyte monitoring system that includes a communication circuit and an analyte sensor configured to generate a signal representative of an analyte concentration level, a processor configured to control operation of the system, and a battery configured to power the system. The method may be implemented, for example, in a system as shown in FIG. 1 or a device as shown in FIG. 2.

The method 800 may include, at 802, receiving a specified time parameter from a peripheral device. The specified time parameter may, for example, be a specified time, such as a specific date (e.g., date, week, or month), or an amount of time, such as a number of days, weeks, or months. The method 800 may further include, at 804 determining an amount of energy remaining in a battery, e.g. based upon a voltage measurement, a current measurement, a coulomb counter, or any combination thereof. The method 800 may further include, at 806, determining a system operating protocol calculated to assure that projected energy consumption by providing an estimated battery life that satisfies the specified time parameter. For example, a projected energy consumption rate may be determined based on one or more communication parameters (e.g., strength of transmissions, how often the system communicates, or how many devices with which the system will communicate), one or more data processing parameters (e.g., how much data processing will occur, and how often it will occur), one or more sensing parameters (e.g., how often a sensor reading will be obtained), or any combination thereof. In an example, the lifetime or expiration of an analyte sensor system (e.g., CGM) may be aligned with or extended to exceed the lifetime or expiration of a pump, e.g., a CGM may be operated to assure that the battery life of the CGM outlast the battery life of the pump or changing of a pump insertion site. In some examples, the system may assure that enough battery remains at the end of the session to perform one or more end-of-session tasks, such as transferring data to an external device such as a smartphone. In some examples, a notification may be delivered to a user to change or check an analyte sensor system battery to coordinate battery replacement with pump replacement or insertion site change.

Figure 9:
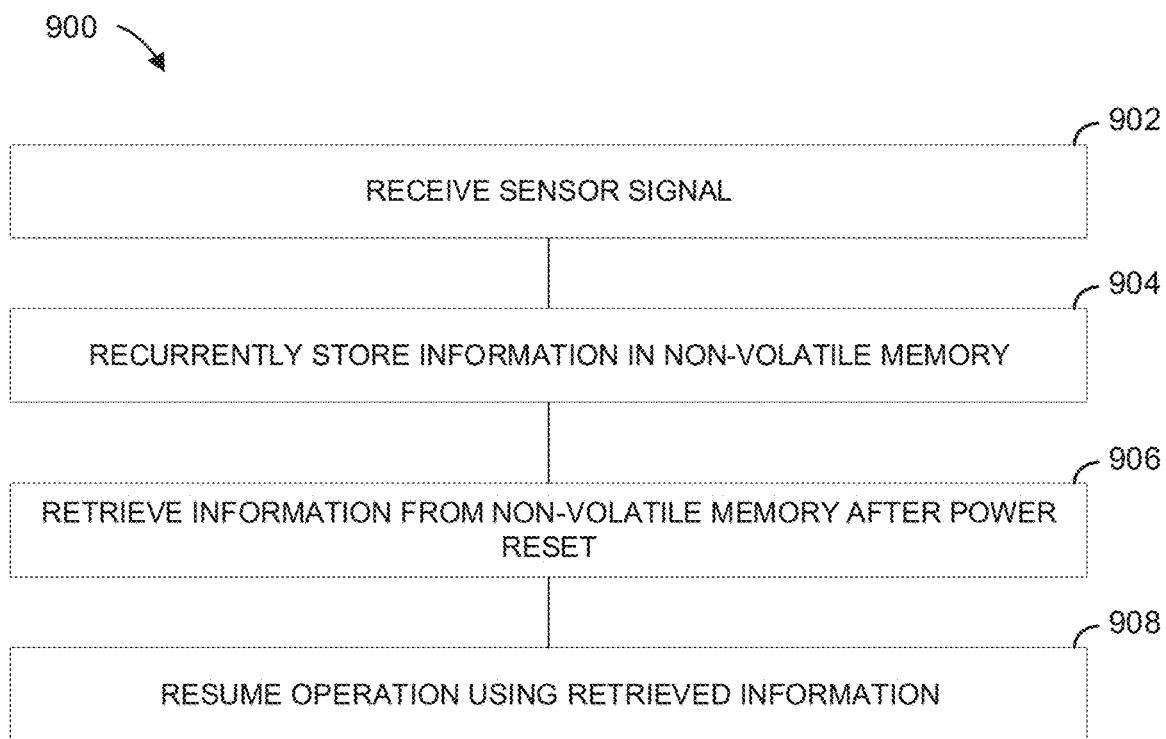
FIG. 9 is a flowchart illustration of an example method of using information from a non-volatile memory after a power reset.

FIG. 9 is a flowchart illustration of an example method 900 of using information from a non-volatile memory after a power reset. The method may be implemented, for example, in a system as shown in FIG. 1 or a device as shown in FIG. 2.

The method 900 may include, at 902, receiving a sensor signal representative of an analyte concentration level from a wearable analyte monitor. The method 900 may further include, at 904, recurrently storing information in a non-volatile memory in preparation for an unplanned power reset, such as when a removeable battery is removed from a device. The stored information may include, for example, an estimated analyte concentration level determined from the sensor signal, and an associated time stamp. In some examples, the method 900 may also include storing time data, session data, pairing information, reset counts, or battery effects of resets in the nonvolatile memory. A reset count and effect of resets may be accounted for in an estimation of battery life remaining.

In some examples, periodically storing information may include storing critical information. Critical information may be used to reestablish a session after a power reset and continue the session according to operating parameters that were in use prior to the power reset. For example, a mode (e.g., communication mode, operating mode of a device, or mode of interaction with a peripheral device such as a pump) or status (e.g., analyte trend or patient status) may be resumed after a power reset.

The method 900 may further include, at 906, retrieving the stored information from the nonvolatile memory after a power reset. In some examples, the method may further include initiating a power-up mode after a power reset and using the stored information to assess device status or an analyte status in the power-up mode. In some examples, a debouncing circuit (e.g., gate with hysteresis) may be used to avoid recurrent execution of a power-up or power down process when a battery is repeatedly connected and disconnected, or avoid processing of noise signal associated with removal or replacement of a battery. In some examples, a system may execute instructions to remove noise associated with removal or insertion of a battery. For example, a system or device may detect connection or disconnection of a battery, and the system may delay a power up or power-down process or delay processing of a signal for a specified period of time after a connection or disconnection from the battery is detected. In some examples, a system or device may delay a power-down process for a specified period of time after a connection to a battery is detected, which may allow the system or device to avoid successive execution of power-up and power-down processes when a battery is connected and disconnected multiple times in a short time window.

The method may further include, at 908, resuming operating using the retrieved information. In some examples, the method may further include determining an operating mode based at least in part on the stored information. In some examples, the determined operating mode may include one or more of a power consumption mode or a communication mode. For example, the system may determine using stored information whether to operate in a low power operating mode, normal operating mode (e.g., default), or high-power operating mode (e.g., high frequency communication or high power to assure range or high probably of communication success, which may be useful for example when the patient is in an unmanaged condition, e.g., in or trending toward a high glucose state or low glucose state.)

In some examples, a low-power mode may be initiated based on a battery condition (e.g., based on current, voltage, or remaining energy) or the amount of battery life remaining (e.g., time until expiration or estimated time until satisfaction of an end-of-life condition). In various examples, the low-power mode may conserve power by communicating less often, or shifting to from a first communication mode or protocol to a second mode or protocol that uses less power (e.g., shift from Bluetooth to NFC), or communicating with fewer devices, or relying on a peripheral device to communicate with another device (e.g., engaging a smartphone to communicate to a watch, pump, or smart pen), or performing a non-communication operation (e.g., sensing) less often, or offloading processing to a peripheral device (e.g., rely on a smartphone for complex processing). In some example, the determination of whether to operate in the low-power mode after a power reset may be based upon battery power after reset (e.g., to detect whether a battery with sufficient power (e.g., new battery) has been inserted, or whether a low-power battery (e.g., the same battery as was removed, or another low-power battery) has been inserted. In some example, a power level assessment (e.g., decision whether to operate in a low-power mode) may be triggered after a power reset based upon information stored before the reset (e.g., based on one or more of the mode of operation before reset, or an analyte management condition (e.g., glucose level or trend), or communication condition (e.g., reliable or not) or communication mode (e.g. 2-way or 1-way.))

In some examples, the method may include determining an analyte trend a based at least in part on an estimated analyte concentration level retrieved from the nonvolatile memory.

In some examples, the method may include periodically saving first information on a first schedule and periodically saving additional information on a second schedule, the first information being saved more frequently than the additional information. For example, information that is critical for resuming a session after a power reset may be saved more frequently than other types of information.

Example Battery and Device Structures

Figure 10A:
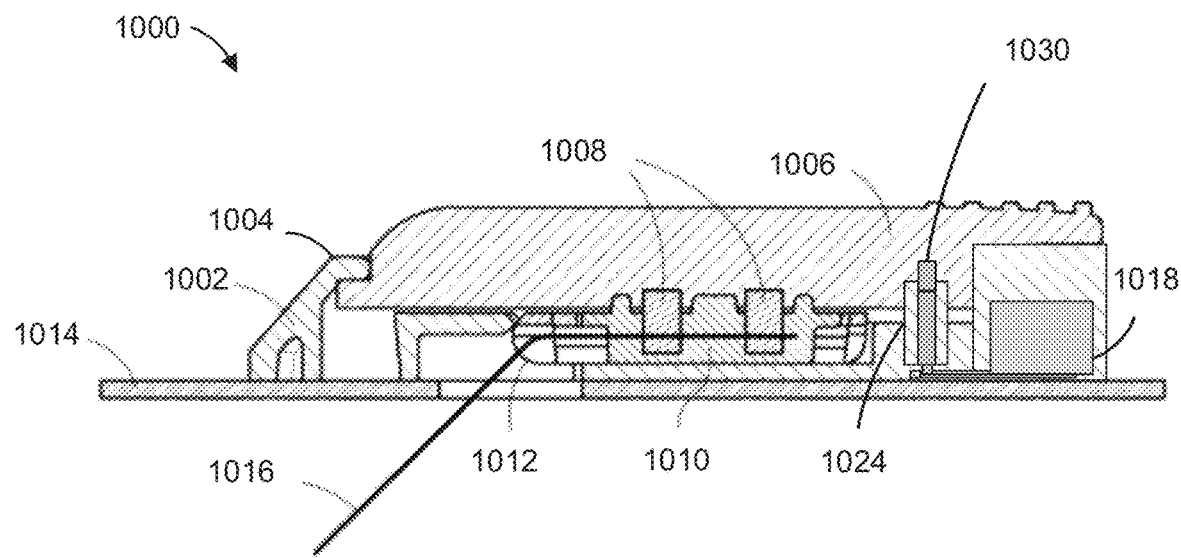
FIG. 10A is a cross sectional view of an example sensor assembly.

FIG. 10A is a cross sectional view of an example sensor assembly 1000. The sensor assembly 1000 may include a base 1002 that may include a mounting unit 1004 that is configured couple with a sensor electronics module 1006, which may be or include the sensor electronics module 106 of FIGS. 1 and 2. The sensor assembly 1000 may also include one or more batteries 1018, which may be removable or replaceable. Battery 1018 may be electrically coupled to an electrical contact 1028, which may be sized and shaped to electrically couple with an electrical contact 1030 on the sensor electronics module 1006, as further explained below.

The base 1002 may include contacts 1008, which may be part of a contact subassembly 1010. The contacts 1008 may be configured to electrically and mechanically contact respective contacts (not shown) on the sensor electronics module, e.g., to enable signal transfer or power transfer. The contact subassembly 1010 may include a hinge 1012 that is configured to allow the contact subassembly 1010 to pivot between a first position (for insertion) and a second position (for use) relative to the mounting unit 1004. The term "hinge" as used herein is a broad term and is used in its ordinary sense, including, without limitation, to refer to any of a variety of pivoting, articulating, and/or hinging mechanisms, such as an adhesive hinge, a sliding joint, and the like; the term hinge does not necessarily imply a fulcrum or fixed point about which the articulation occurs. In some examples, the contacts 1008 may be formed from a conductive elastomeric material, such as a carbon filled elastomer, in electrical connection with the sensor 1016.

In some examples, the mounting unit 1004 may be provided with an adhesive pad 1014, disposed on the mounting unit's back surface. The adhesive pad may include a releasable backing layer. The mounting unit 1004 may be adhered to the skin of a host by pressing the base 1002 of the mounting unit and the adhesive pad 1014 onto the skin. Appropriate adhesive pads can be chosen and designed to stretch, elongate, conform to, and/or aerate the region (e.g., host's skin). Various configurations and arrangements can provide water resistant, waterproof, and/or hermetically sealed properties associated with the mounting unit/sensor electronics module embodiments described herein. Any of the examples discussed herein may be sealed to avoid, for example, exposure to water or excessive exposure to moisture.

Figure 10B:
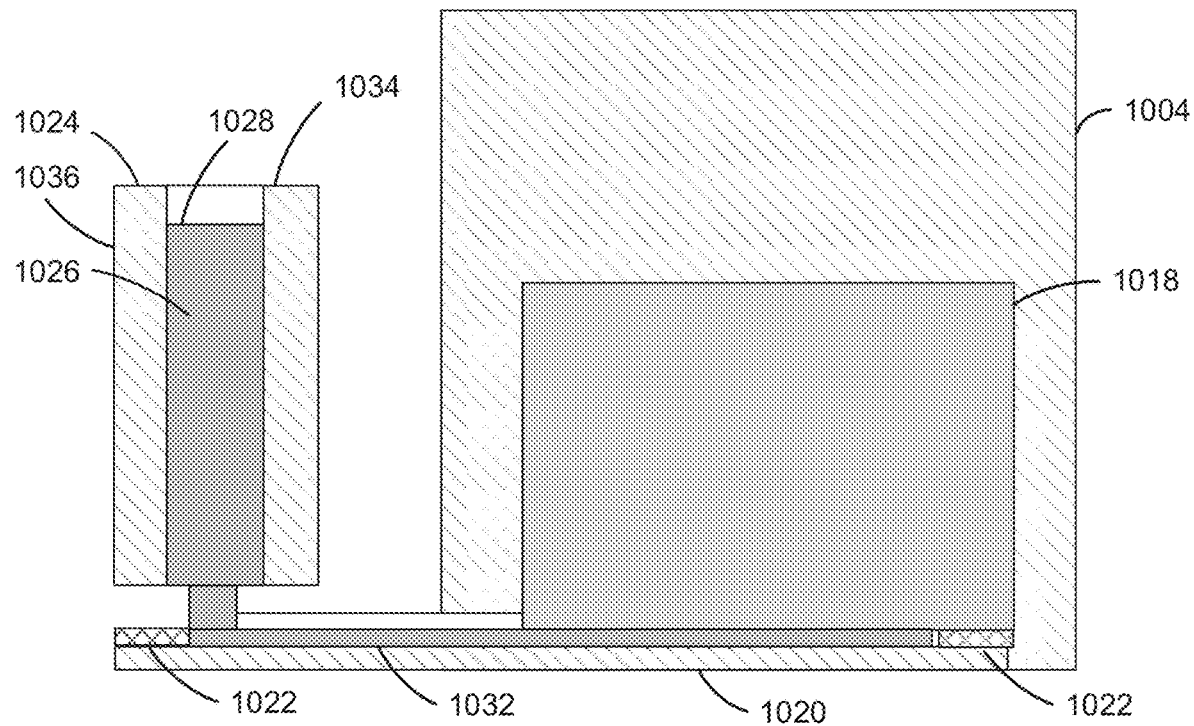
FIG. 10B is an enlarged portion of the sensor assembly of FIG. 10A.

FIG. 10B is an enlarged view of a portion of the sensor assembly of FIG. 10A. The base 1002 may be configured to receive one or more batteries 1018, which may for example be coin cell batteries (e.g. silver oxide, lithium, alkaline, zinc air, etc.). A sealed region 1020 may extend over the batteries to isolate and secure the batteries 1018 in the base 1002. In various embodiments, the sealed region may be coupled to the base using mechanical connections (e.g. snap fit), adhesives, welded joints, or any combination thereof.

The base 1002 may include one or more protrusions 1024 (e.g., seal member or seal feature) that extend upward to the sensor electronics module 1006. Electrical connector 1026 may extend through the protrusion 1024 and electrically connect via electrical contact 1028 with a second electrical contract 1030 on the sensor electronics module 1006. In some examples, an end surface 1034 of the protrusion 1024 (seal member) may seal against an opposing surface on the sensor electronics module to form a seal (e.g., face seal.) In some examples, an outer side surface 1036 of the protrusion 1024 may seal against a corresponding surface (e.g., an inner surface on a cavity on sensor electronics module 1006) to form a radial seal (e.g., an O-ring or lip seal against the sensor electronical module.)

In the example shown in FIGS. 10A and 10B, the protrusion 1024 and electrical connector 1026 are laterally offset from the one or more batteries (i.e., to the right of the battery in FIG. 10B), in which case the electrical connector 1026 may be electrically coupled with the battery via electrical connector 1032. In some alternative examples, such as the embodiment shown in FIG. 13A, the protrusions may extend upward from batteries, as shown, for example, in FIG. 11A.

The protrusions 1024 may form a seal with the sensor electronics module 1006 when the sensor electronics module is assembled with the base 1002. For example, the protrusions may form a radial seal or face seal with the sensor electronics module 1006. The protrusions may be overmolded to a base or over or around the electrical contact 1028. Alternatively, a seal component may be coupled to the protrusion (e.g., the protrusion itself may be integral with the base and a seal component may be overmolded to the base or otherwise coupled to or placed around the protrusion). The protrusions or seal may be formed of a material to form a watertight seal, such as an elastomeric or conformable material (e.g., Silicone, TPE, Polypropylene, etc.).

Each of the example bases shown in FIGS. 10A through 21B may include one or more electrical contacts 1028, 1029 that may be configured to deliver battery power to a sensor electronics module (e.g., sensor electronics module 106 or sensor electronics module 1006, not shown in FIGS. 11A-21B). While the examples are shown with two batteries, other examples may include a single battery, or more than two batteries (e.g., three, four, or more batteries.) In various examples, the batteries may all be the same, or the batteries may be sized differently, or may have difference electrical or electrochemical properties to provide desired performance characteristics (e.g., current capacity or battery life.) In examples with two or more batteries, the batteries may be arranged in series or parallel, but preferably in series, so that one contact 1028 is positive and the other contact 1029 is negative (or vice-versa) to thereby form a closed circuit when coupled with the sensor electronics module. The base may also include electrical contacts 1008, 1010, which may be configured to interface with the sensor electronics module to operatively couple one or more sensor system components (e.g., potentiostat 202 shown in FIG. 2) to supply power to generate a sensor signal (e.g., to apply a bias to via sensor 1016 to generate a signal indicative of an analyte concentration level). In some examples, a cover, film, flex circuit substrate, potting material (e.g. epoxy), or other component may be provided and configured to extend over the batteries and seal with the base. A sealed interface may be created using one or more of a seal component (e.g. O-ring or elastomer), ultrasonic welding, laser, radiofrequency (RF), or heat welding. A sensor electronics seal may also be provided between the sensor electronics module 1006 and the base. In any of the examples shown in FIGS. 10A-22B, the batteries may be coupled to a sensor electronics package via conductive elastomer contacts (e.g. pucks), springs, tabs, posts, or other conductive materials, which may in various configurations be affixed to the base, or to a sensor electronics module. Any of the structural elements shown in FIGS. 10A-22B may be combined with an example shown in another of the FIGS. 10A-22B, and many of the examples may have similar or identical components, as shown in the drawings.

A battery seal may be provided between the sensor electronics module and the batteries or battery contacts, for example to avoid contact between the batteries and the outside environment (e.g., water during swimming or bathing), which may corrode, deplete, or damage the batteries or electronic components. The battery seal may, for example, be a face seal, radial seal (e.g., O-ring), or an irregular seal. The seal may, for example, include an overmolded component such as an overmolded gasket, an overmolded elastomeric feature that may be coupled to or assembled with the base or sensor electronics module, or other overmolded or assembled seal components or features. The seal or seals may create one continuous seal around the perimeter of both batteries (e.g., see FIGS. 12A and 15A, 16A, 18A, and 19A), or may create a seal around each battery individually (e.g., see FIGS. 11A, 13A, and 14A). In various configurations, the batteries 1018 may be assembled into the base through the bottom of the base (e.g., see FIGS. 11A and 11B, 13A-16B, and 20A-22B), or through the top of the base (e.g., see FIGS. 12A and 12B, and 17A-19B).

Any of the examples shown in FIGS. 11A through 21B may be coupled to an adhesive component such as adhesive pad 1014 shown in FIG. 10A, or alternatively or additionally may include adhesive on the bottom surface 1052 of the base, to couple the base to a host.

Figures 11A, 11B:
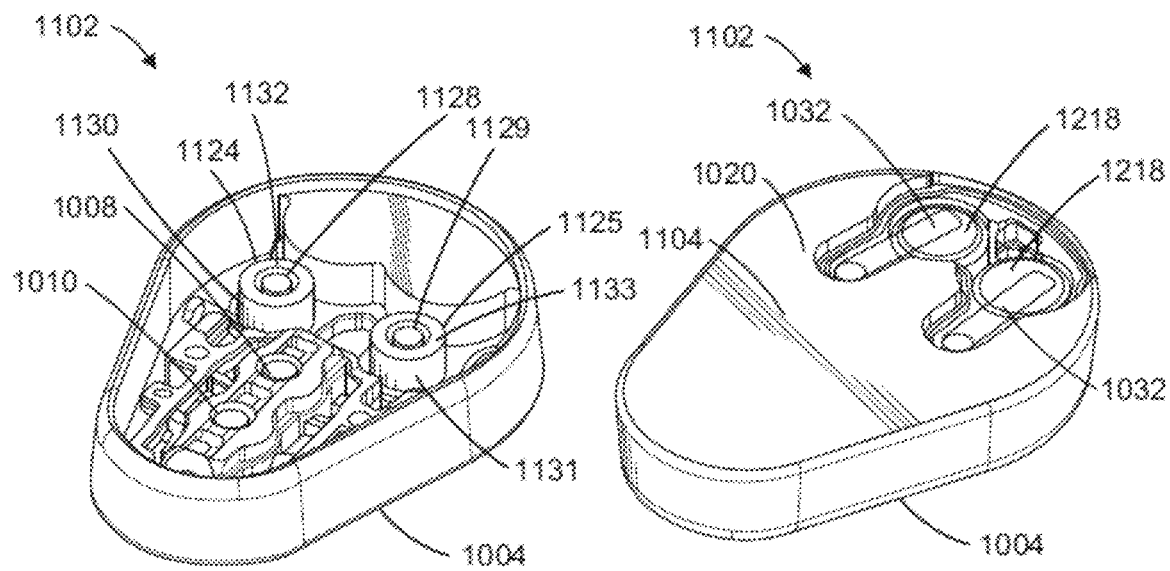
FIG. 11A is a perspective top view of an example sensor base.
FIG. 11B is a perspective bottom view of the base shown in FIG. 11A.

FIG. 11A is a perspective top view of an example sensor base 1102 that has two protruding seal members 1124, 1125, which may be offset from batteries 1018. FIG. 11A shows electrical contacts 1128, 1129 as conductive elastomeric puck style contacts that may press against corresponding contacts (not shown) on the sensor electronics modules when the sensor electronics module is assembled with the base 1102. Battery power may be supplied to the sensor electronics module via electrical contacts 1128, 1129. The seal members 1124, 1125 may be configured to seal against a sensor electronics module (not shown) so that electrical contacts 1128, 1129 may be sealed from exposure to potential environmental elements, such as water. The seal members 1124, 1125, may, for example be overmolded elastomeric seal (e.g., overmolded onto the base.) The seal members 1124 may form a face seal when pressed against sensor electronics module. In an example, the outer side surfaces 1130, 1131 of the sensor electronics module may seal against one or more inner surfaces of corresponding cavities in the sensor electronics module. Alternatively or additionally, end surfaces 1132, 1133 may form a seal against opposing surfaces on the sensor electronics module.

FIG. 11B is a perspective bottom view of the base 1102. The batteries 1018 may be sealed in the base. In some examples, the analyte sensor 1016 (not shown in FIG. 11B) may be delivered through the bottom surface 1104 of the base 1102 and into a host, e.g., through a hole (not shown in FIG. 11B) in the sealed region 1020 (e.g., cover.) The analyte sensor 2016 may, for example, be delivered via a mechanical or electrical delivery system (e.g., applicator, not shown), which may, for example, be configured to insert a needle/sensor assembly into a host and withdraw the needle to leave the sensor in the host for sensing an analyte (e.g., glucose) concentration. Example sensor delivery systems are shown and described in U.S. Pat. No. 7,949,381, U.S. patent application Ser. No. 15/387,088 (published as US20170188910A1), and U.S. patent application Ser. No. 15/298,721 (published as US20170112534A1) which are incorporated by reference. Any of the examples shown in FIGS. 11A-22A may similarly configured to receive a sensor 1016 and sensor delivery system.

The base 1102 and the bases shown in FIGS. 12A-22 may include a mounting unit 1004, electrical contacts 1008, 1010, and a sealed region 1020, as described in reference to FIGS. 10A and 10B.

Figures 12A, 12B:
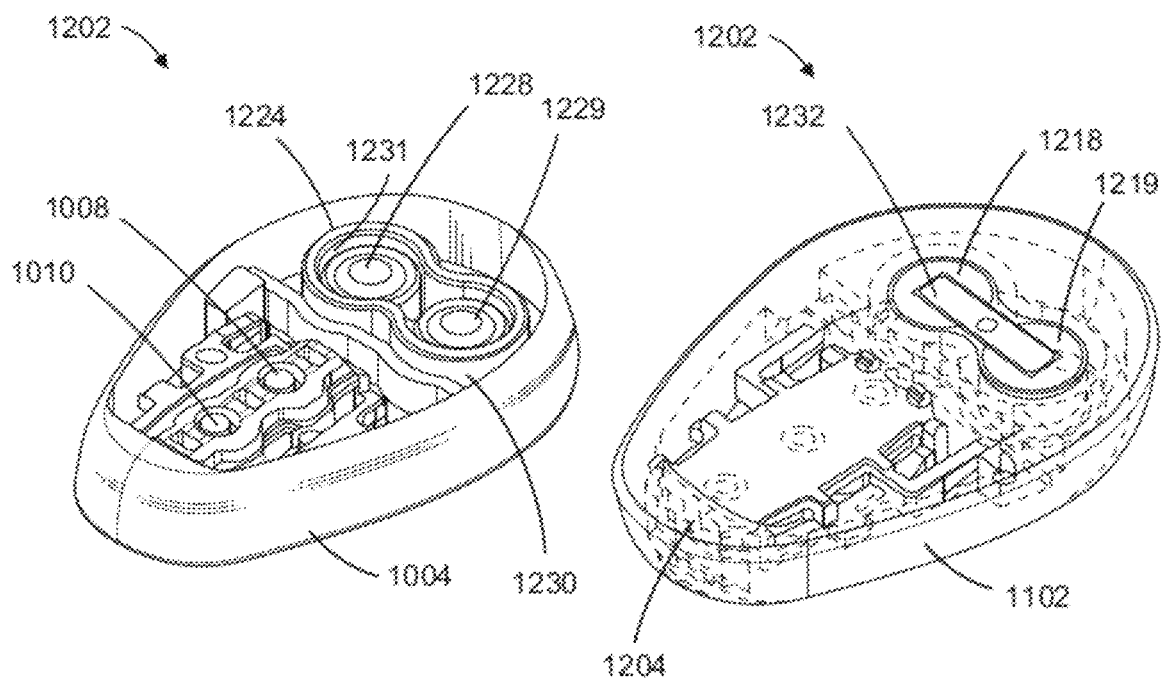
FIG. 12A is a perspective top view of an example sensor base.
FIG. 12B is a perspective bottom view of the base shown in FIG. 12A.

FIGS. 12A and 12B illustrate an example base 1202 that in which batteries may be loaded from a top side as opposed to a bottom side as shown in FIG. 11B. A seal member 1224 may extend around both batteries 1218, 1219 and optionally also around battery contacts 1228, 1229. Battery contacts 1228, 1229 may be separate parts, or may be a portion of a battery. The seal member 1224 may be overmolded to the base or assembled with the base and placed around battery contacts 1228, 1229, or around the battery contacts 1228, 1229 and the batteries 1018. An outer surface 1230 of the seal member 1224 may be configured to seal against an opposing internal surface (e.g., inner surface of a cavity) on the sensor electronics module (e.g., sealed against inner surface 1952 on sensor electronics module 1904 in FIG. 19B). Additionally or alternatively, an inner surface 1231 of the seal member 1224 may be configured to seal against an opposing surface on the sensor electronics module. As shown in FIG. 12B, the batteries 1218, 1219 may be electrically coupled via connector 1232. A sensor (e.g., sensor 104 or sensor 1016) may be delivered via a passageway in the base such as the hole 1240 shown in FIG. 12B.

Figures 13A, 13B:
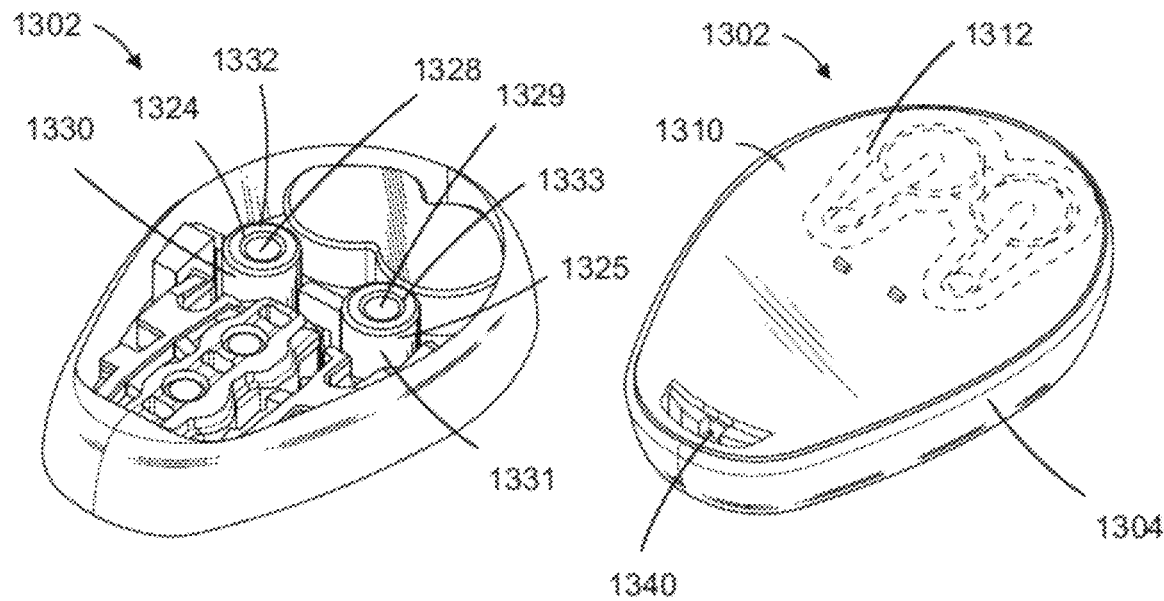
FIG. 13A is a perspective top view of an example sensor base.
FIG. 13B is a perspective bottom view of the base shown in FIG. 13A.

FIGS. 13A and 13B illustrate an example base 1302 that includes seal members 1324, 1325 having side surface 1330, 1331 that may form a face seal with corresponding surfaces on the sensor electronics module (e.g. seal against inner surfaces of a cavity on sensor electronics module) to seal battery electrical contacts 1328 1329 against exposure to water or moisture. Additionally or alternatively, the end surfaces 1332, 1333 may form a seal against the sensor electronics module.

FIG. 13B shows a film 1310 (or alternatively flex circuit substrate) that may be laser or heat bonded (e.g., glued or welded) to the mounting unit 1304 to seal the batteries in the mounting unit 1304. For example, a sealed path 1312 may be laser bonded or heat bonded around the batteries to create an isolated region around the batteries. A sensor (e.g., sensor 104 or sensor 1016) may be delivered via a passageway in the base such as the hole 1340 shown in FIG. 13B.

Figures 14A, 14B:
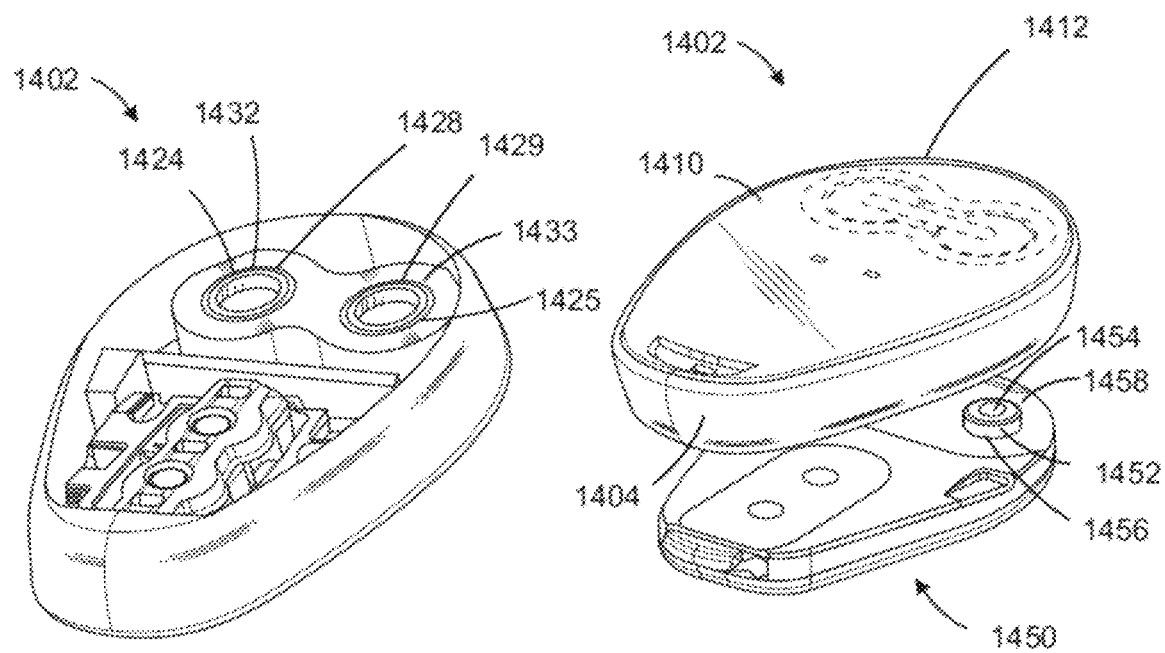
FIG. 14A is a perspective top view of an example sensor base.
FIG. 14B is a perspective bottom view of the base shown in FIG. 14A and an example sensor electronics module configured to mechanically and electrically couple with the base shown in FIGS. 14A and 14B.

FIGS. 14A and 14B illustrate an example base 1402 and sensor electronics module 1450. The sensor electronics module may include one or more protrusions 1452 (e.g., second protrusion is behind base and thus not shown) that include one or more electrical contacts 1454 that is configured to electrically couple with electrical contacts 1428, 1429 on the base 1402. Protrusion 1452 may be configured to fit into corresponding recesses 1434, 1435 in seal members 1424, 1425 so that one or more outer surfaces 1456 on the protrusion form a radial seal with seal members.

The seal members 1424, 1425 may also optionally have end surfaces 1432, 1433 that may be sized and shaped to form seal against an opposing surface 1458 on the sensor electronics module to further seal battery electrical contacts 1428 1429 against exposure to water or moisture.

FIG. 14B shows a film 1410 (or alternatively flex circuit substrate) that may be laser or heat bonded to the mounting unit 1404 to seal the batteries in the mounting unit 1404. For example, a sealed weld path 1412 may be laser bonded or heat bonded around the batteries to create an isolated region around the batteries.

Figure 15A:
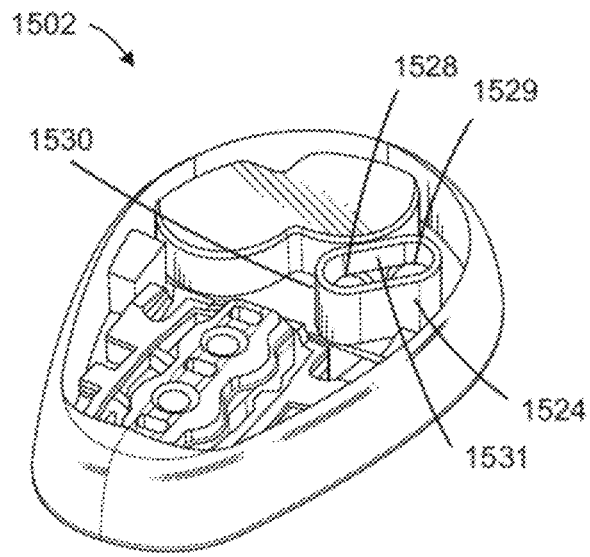
FIG. 15A is a perspective top view of an example sensor base.
Figure 15B:
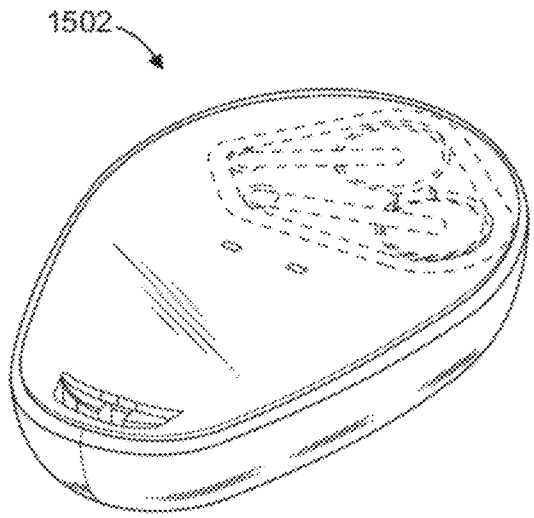
FIG. 15B is a perspective bottom view of the base shown in FIG. 15A.

FIGS. 15A and 15 B illustrate an example base 1502 having a seal member 1524 that may extend around one or more battery contacts 1528, 1529. An outer surface 1530, inner surface 1531, or both, may be configured to seal against corresponding opposing surfaces on a sensor electronics module (not shown in FIG. 15A, 15B to form a seal around both battery contacts. The seal member 1524 may, for example, be an overmolded elastomeric gasket.

Figure 16A:
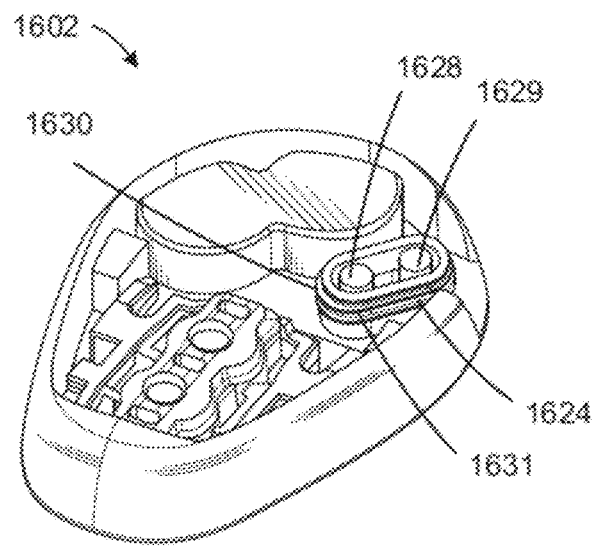
FIG. 16A is a perspective top view of an example sensor base.
Figure 16B:
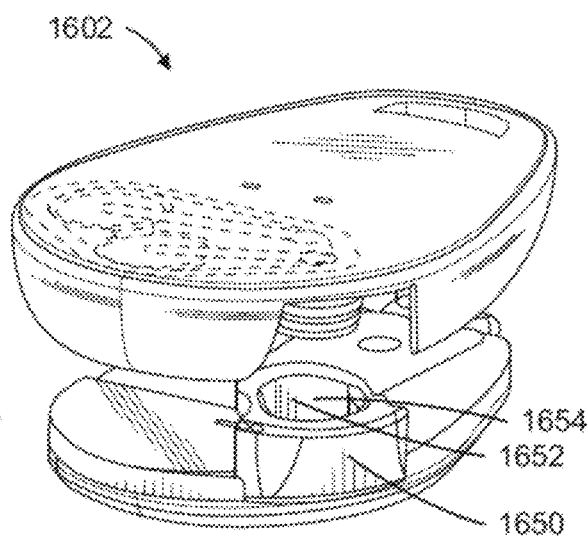
FIG. 16B is a perspective bottom view of the base shown in FIG. 16A and an example sensor electronics module configured to mechanically and electrically couple with the base shown in FIGS. 16A and 16B.

FIGS. 16A and 16 B illustrate an example base 1602 having a seal member 1624 that may extend around one or more battery contacts 1628, 1629. An outer surface 1630 of the seal member may include one or more ribs 1631 that may form a radial seal (e.g., similar to an O-ring) with an inner surface 1652 of a cavity 1654 formed by the sensor electronics module 1650. The seal member 1624 may, for example, be a molded elastomeric seal placed over the battery contacts 1628, 1629. In another example, the seal member 1624 may be overmolded onto the base.

Figure 17A:
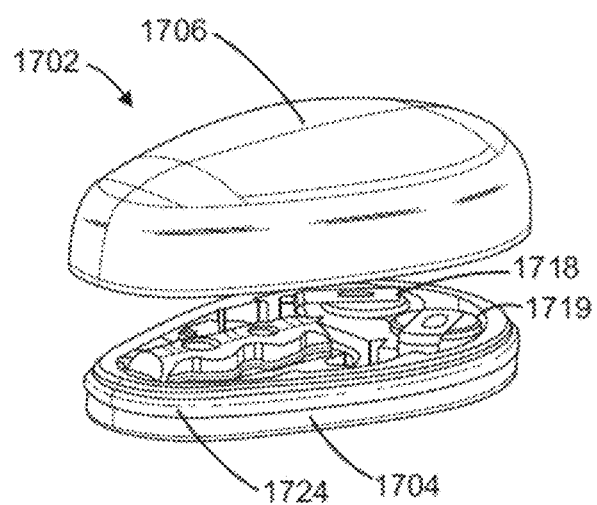
FIG. 17A is an exploded (disassembled) perspective top view of an example sensor base and example sensor electronics module.
Figure 17B:
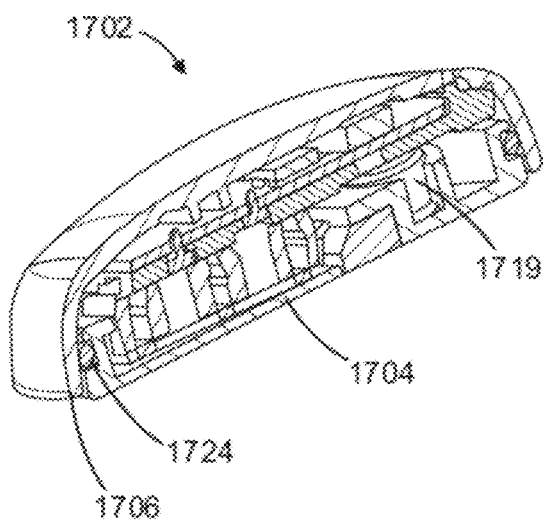
FIG. 17B is a perspective view of the base shown in FIG. 17A assembled with the sensor electronics module.

FIGS. 17A and 17B illustrate an example base 1702 that includes a radial seal (e.g., O-ring seal) that extends around a bottom component 1704 of the base. The radial seal 1724 and a top component 1706 (which may be a portion of a sensor electronics module) may be configured to form a fluid-tight seal to avoid exposure to water or moisture.

Figure 18A:
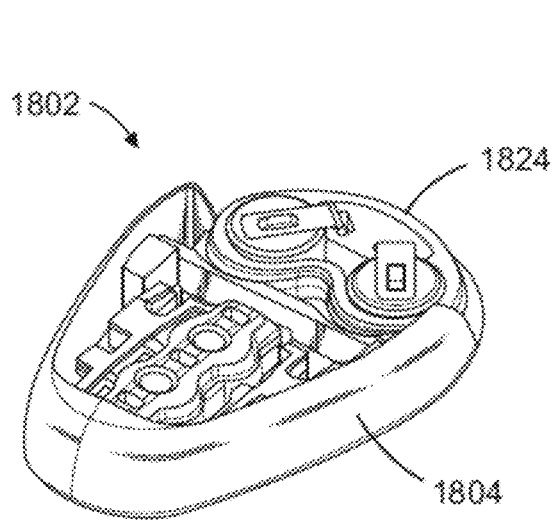
FIG. 18A is a perspective top view of an example sensor base.
Figure 18B:
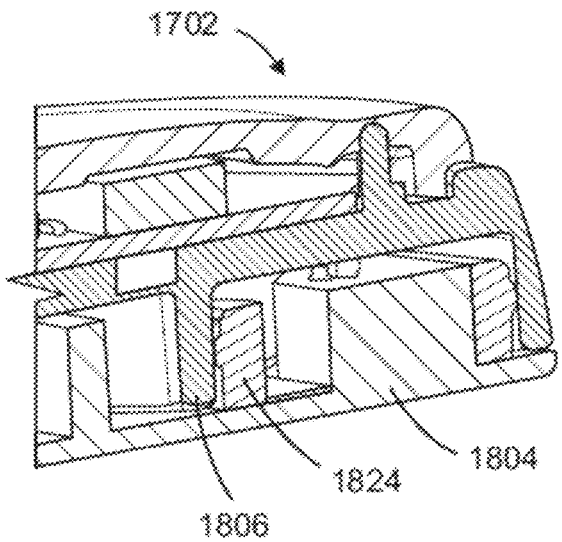
FIG. 18B is an enlarged perspective view of the base shown in FIG. 17A assembled with an example sensor electronics module.

FIGS. 18A and 18B illustrate an example base 1802 that includes a radial seal that extends around a bottom component 1804 of the base. The radial seal 1824 and a portion 1806 of a sensor electronics module may be configured to form a fluid-tight seal to avoid exposure to water or moisture. The radial seal 1824 may, for example, be or include an overmolded elastomeric feature (e.g., overmolded onto the base so that it extends around inserted batteries or battery contacts).

FIGS. 19A and 19B illustrate an example base 1902 that includes a seal member 1924 that extends around both batteries 1918, 1919. The seal member 1924 may be overmolded to the base, and sized and shaped to extend around batteries 1918, 1919 (or around the battery contacts (not shown) and the batteries). An outer surface 1930 of the seal member 1924 may include a ring feature 1931 that may be configured to seal against an opposing internal surface 1954 in a cavity on sensor electronics module 1950.

FIGS. 20A and 20B illustrate another example base 2002 that includes a single seal member 2024 that may include a cavity 2126 that may be configured to receive a protrusion 2052 extending from a bottom side 2054 of a sensor electronics module 2050. The seal member 2024 may be configured to seal against an outer surface 2058 of a protrusion. In some examples, the seal member 2024 may form a face seal with the protrusion 2052, or may form a radial seal (e.g., via an internal rib (not shown) in the cavity 2026 on the seal member). The protrusion 2052 may include one or more electrical contacts 2056 (e.g., a second contact, not shown, may be on the other side of the protrusion to complete a circuit, see, e.g., FIG. 21B.) The electrical contacts 2056 may electrically couple with corresponding contacts (not shown) on an inside surface of the seal member 2024 (e.g., on the walls inside the cavity 2026 on the seal member 2024 that receives the protrusion.

Figures 21A, 21B:
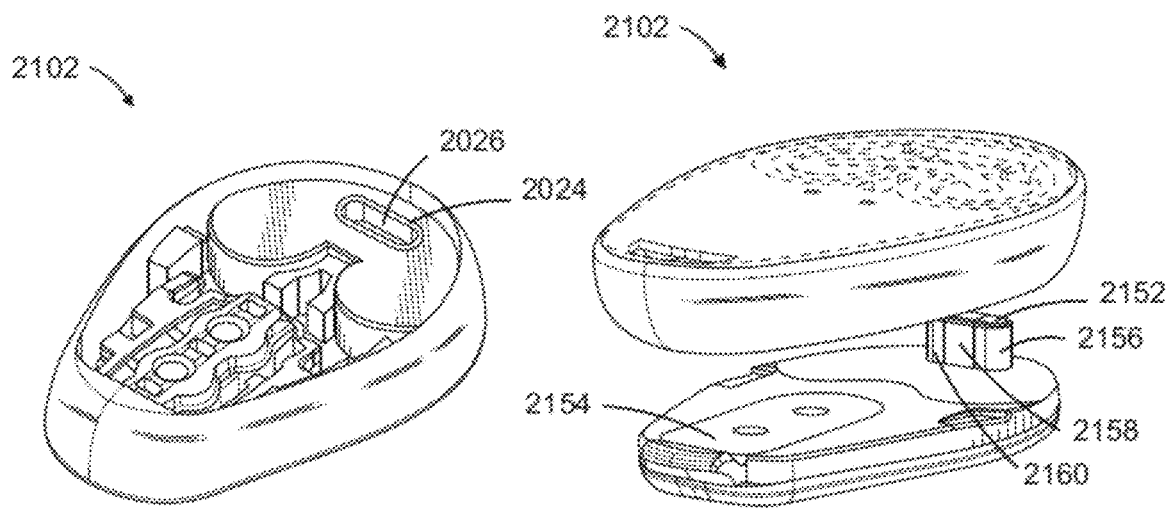
FIG. 21A is a perspective top view of an example sensor base.
FIG. 21B is a perspective bottom view of the base shown in FIG. 21A and an example sensor electronics module configured to mechanically and electrically couple with the base shown in FIGS. 21A and 21B.

FIGS. 21A and 21B illustrate another example base 2102 that includes a single seal member 2124 that may include a cavity 2126 that may be configured to receive a protrusion 2152 extending from a bottom side 2154 of a sensor electronics module 2150. The seal member 2124 may be configured to seal against an outer surface 2158 of a protrusion. In various examples, the seal member 2124 may form a face seal with the protrusion 2152, or may form a radial seal (e.g., via an internal rib (not shown) in the cavity 2126 on the seal member). The protrusion 2152 may include one or more electrical contacts 2156, 2160. The electrical contacts 2156, 2160 may electrically couple with corresponding contacts (not shown) on an inside surface of the seal member 2124 (e.g., on the walls inside the cavity 2126 on the seal member 2124 that receives the protrusion.)

Figures 22A, 22B:
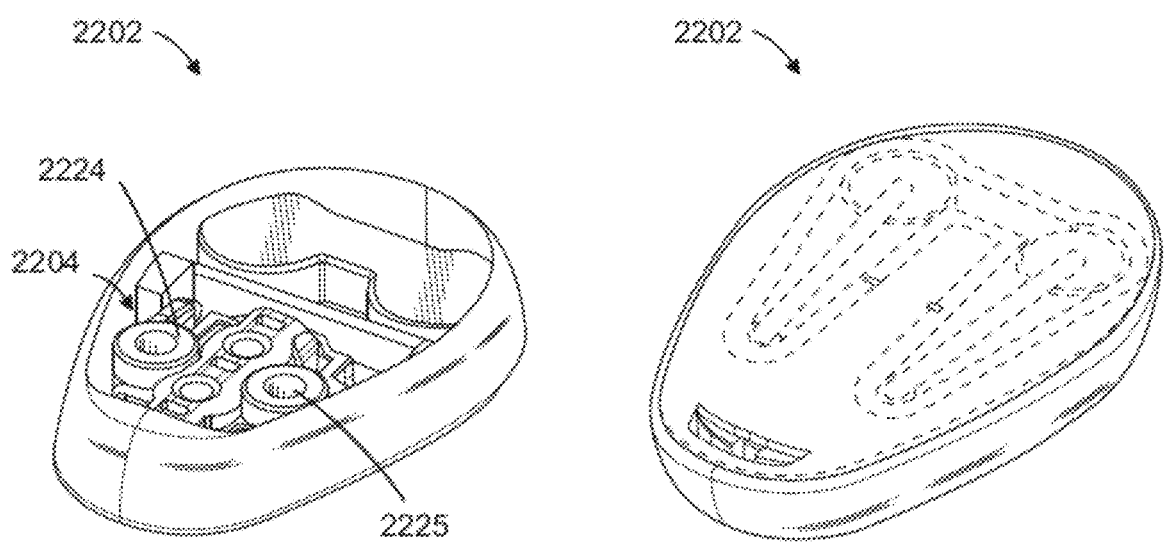
FIG. 22A is a perspective top view of an example sensor base.
FIG. 22B is a perspective bottom view of the base shown in FIG. 22A.

FIGS. 22A and 22B illustrate another example base 2202 that is similar to the example 1102 shown in FIG. 11A, but in which seal members 2224, 2225 are situated in a front portion 2204 o the base 2202.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round", a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. An analyte monitoring system comprising:
an analyte sensor configured to generate a sensor signal representative of an analyte concentration level of a host;
a communication circuit configured to transmit a wireless signal in a first communication mode and a second communication mode to a peripheral device; and
a processor, wherein the processor:
determines whether a first condition is satisfied, the first condition relating to a requirement of the peripheral device associated with a first medicament delivery state of the peripheral device, and shifts the system to a second communication mode responsive to the first condition being satisfied, wherein during the first medicament delivery state the peripheral device does not deliver medicament;
determines whether a second condition is satisfied, wherein the second condition is satisfied when the peripheral device is in or shifts into a second medicament delivery state during which the peripheral device delivers medicament; and shifts from the second wireless communication mode back to the first wireless communication mode responsive to the second condition being satisfied, wherein the shift from the second communication mode back to the first communication mode is associated with an increase in power output from the communication circuit.

2. The analyte monitoring system of claim 1, wherein the system includes a base configured to couple to a host, the base including the analyte sensor, and a sensor electronics package configured to couple to the base, the sensor electronics package including the communication circuit and the processor.

3. The analyte monitoring system of claim 1, wherein the system includes a disposable base configured to couple to the host and a reusable sensor electronics package coupled to the base, the sensor electronics package including the communication circuit.

4. The analyte monitoring system of claim 1, wherein the peripheral device is an insulin delivery device.

5. A method of managing power consumption in an analyte monitoring system configured to communicate with a peripheral device, the method comprising:

receiving from an analyte sensor an analyte signal representative of an analyte concentration level;

determining whether a first condition is satisfied, the first condition relating to a requirement of the peripheral device associated with a first medicament delivery state of the peripheral device, wherein during the first medicament delivery state the peripheral device does not deliver medicament;

responsive to the first condition being satisfied, shifting from a first wireless communication mode to a second wireless communication mode and transmitting a wireless signal relating to the analyte signal using the second wireless communication mode;

determining whether a second condition is satisfied, wherein the second condition is satisfied when the peripheral device is in or shifts into a second medicament delivery state during which the peripheral device delivers medicament; and responsive to the second condition being satisfied, ceasing using the second wireless communication mode and shifting from the second wireless communication mode back to the first wireless communication mode, wherein the shift from the second communication mode back to the first communication mode is associated with an increase in power output of the communication circuit.

6. The method of claim 5, wherein the first wireless communication mode is a continuous connection mode and the second wireless communication mode is a periodic connection mode.

7. The method of claim 5, wherein a processor operatively coupled to the analyte sensor determines whether the first condition is satisfied.

8. The method of claim 5, wherein the peripheral device is an insulin delivery device.

* * * * *